(12) United States Patent
Papay

(10) Patent No.: US 10,322,279 B2
(45) Date of Patent: Jun. 18, 2019

(54) SURGICAL GUIDE AND METHOD FOR GUIDING A THERAPY DELIVERY DEVICE INTO THE PTERYGOPALATINE FOSSA

(71) Applicant: THE CLEVELAND CLINIC FOUNDATION, Cleveland, OH (US)

(72) Inventor: Francis A. Papay, Westlake, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 715 days.

(21) Appl. No.: 14/955,075

(22) Filed: Dec. 1, 2015

(65) Prior Publication Data

US 2016/0106974 A1 Apr. 21, 2016

Related U.S. Application Data

(62) Division of application No. 12/688,300, filed on Jan. 15, 2010, now Pat. No. 9,211,133.

(60) Provisional application No. 61/145,122, filed on Jan. 16, 2009.

(51) Int. Cl.
*A61N 1/00* (2006.01)
*A61N 1/05* (2006.01)
(Continued)

(52) U.S. Cl.
CPC ............ *A61N 1/0548* (2013.01); *A61B 17/24* (2013.01); *A61N 1/0526* (2013.01);
(Continued)

(58) Field of Classification Search
CPC .. A61N 1/0526; A61N 1/0548; A61N 1/0551; A61N 1/36075; A61N 1/375; A61N 1/37205; A61B 17/3468; A61B 17/02; A61B 17/24; A61B 17/3211; A61B 2017/320052; A61B 17/0218

See application file for complete search history.

(56) References Cited

U.S. PATENT DOCUMENTS

| | | | |
|---|---|---|---|
| 5,558,622 | A | 9/1996 | Greenberg |
| 6,093,145 | A | 7/2000 | Vom Berg et al. |
| (Continued) | | | |

FOREIGN PATENT DOCUMENTS

| | | |
|---|---|---|
| WO | 2003082123 A2 | 10/2003 |
| WO | 2008066557 A1 | 6/2008 |

OTHER PUBLICATIONS

The PCT International Search Report dated Mar. 30, 2010 for PCT International Application No. PCT/US2012/021169, filed Jan. 15, 2010.

(Continued)

*Primary Examiner* — Lindsey G Wehrheim
(74) *Attorney, Agent, or Firm* — Tarolli, Sundheim, Covell & Tummino LLP

(57) ABSTRACT

A surgical guide to facilitate delivery of a therapy delivery device into the pterygopalatine fossa of a subject includes a curvilinear body having a distal end portion, a proximal end portion, and an intermediate portion extending between the distal and proximal end portions. The proximal end portion is defined by oppositely disposed first and second surfaces. The proximal end portion and the intermediate portion define a longitudinal plane that extends between the proximal and distal end portions. The distal end portion has an arcuate configuration relative to the longitudinal plane and is defined by oppositely disposed third and fourth surfaces.

30 Claims, 23 Drawing Sheets

(51) Int. Cl.
    *A61N 1/36*         (2006.01)
    *A61B 17/24*       (2006.01)
    *A61B 17/02*       (2006.01)
    *A61B 17/3211*    (2006.01)
    *A61B 17/32*       (2006.01)

(52) U.S. Cl.
    CPC ....... *A61N 1/0558* (2013.01); *A61N 1/36057*
          (2013.01); *A61B 17/02* (2013.01); *A61B*
          *17/3211* (2013.01); *A61B 2017/320052*
          (2013.01); *A61N 1/3606* (2013.01)

(56) References Cited

U.S. PATENT DOCUMENTS

| | | |
|---|---|---|
| 6,149,657 A | 11/2000 | Kuzma |
| 2004/0220644 A1 | 11/2004 | Shalev et al. |
| 2006/0111754 A1 | 5/2006 | Rezai et al. |
| 2006/0178666 A1 | 8/2006 | Cosman et al. |
| 2006/0195169 A1 | 8/2006 | Gross et al. |
| 2006/0293723 A1 | 12/2006 | Whitehurst et al. |
| 2008/0172102 A1 | 7/2008 | Shalev |
| 2010/0168513 A1 | 7/2010 | Pless et al. |
| 2016/0081716 A1* | 3/2016 | Boling .................. A61B 17/24 606/129 |

OTHER PUBLICATIONS

Theodosopoulous et al., "Endoscopic Approach to the Infratemporal Fossa: Anatomic Study", Neurosurgery 66: 196-203, 2010.

* cited by examiner

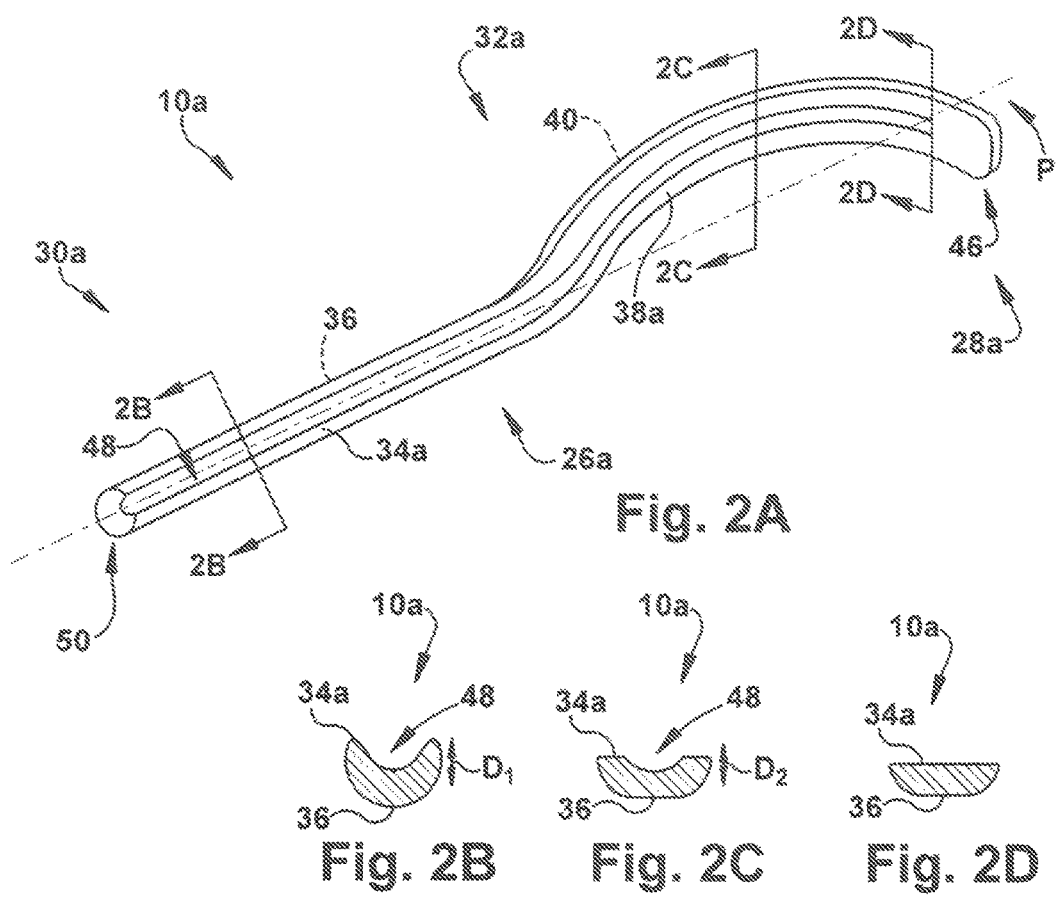
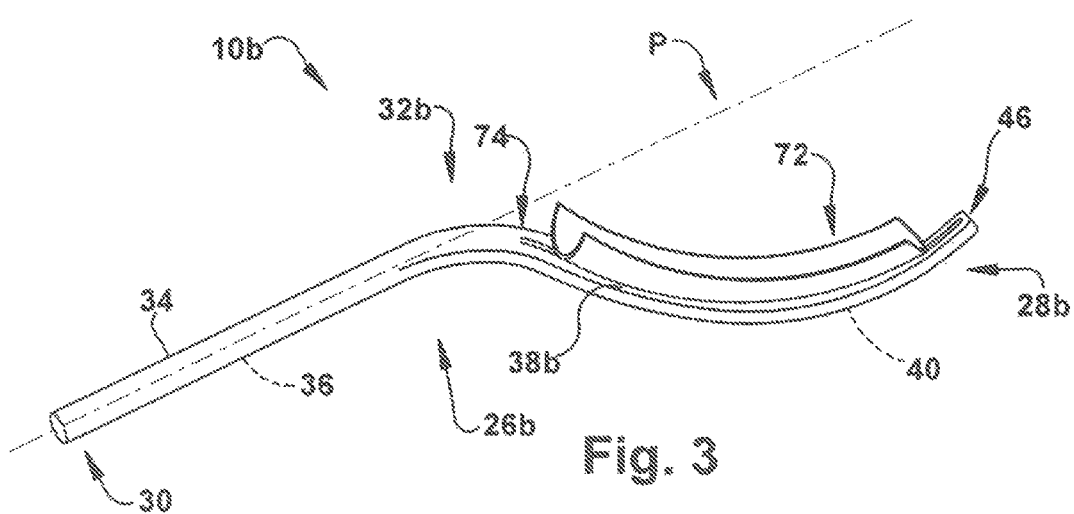

SURGICAL GUIDE AND METHOD FOR GUIDING A THERAPY DELIVERY DEVICE INTO THE PTERYGOPALATINE FOSSA

RELATED APPLICATION

This application is a divisional application of U.S. patent application Ser. No. 12/688,300, filed Jan. 15, 2010, which claims priority from U.S. Provisional Patent Application No. 61/145,122, filed Jan. 16, 2009 (Now Expired), the entirety of each of which is hereby incorporated by reference.

TECHNICAL FIELD

The present invention relates generally to an apparatus and method for delivering therapy delivery devices to craniofacial locations, and more particularly to a surgical guide and method for delivering a therapy delivery device into the pterygopalatine fossa of a subject.

BACKGROUND OF THE INVENTION

Headaches are one of the most common ailments, and afflict millions of individuals. The specific etiology of headaches may be difficult to pinpoint. Known sources of headache pain include trauma and vascular, autoimmune, degenerative, infectious, drug and medication-induced, inflammatory (sarcoid), neoplastic (primary or metastatic), metabolic-endocrine, iatrogenic (such as post-surgical), muscloskelatal and myofascial causes. Even if the condition underlying the headache pain is identified and treated, headache pain may persist.

Currently, the sphenopalatine ganglion (SPG) is a target of manipulation in clinical medicine to treat headaches. The SPG is a neuronal center located outside of the brain behind the nose. It consists of parasympathetic neurons innervating the middle cerebral and anterior cerebral lumens (in part), the facial skin blood vessels, and the lacrimal glands. Manipulation of the SPG is mostly performed in attempted treatments of severe headaches, such as cluster headaches.

Various clinical approaches have been used to modulate SPG function and treat headaches. These procedures vary from least invasive (e.g., sphenopalatine blocks using lidocane or cocaine, which provide 30%-85% relief of pain on a temporary basis) to much more invasive (e.g., surgical resection of the SPG, radiofrequency gangliorhizolysis, and gamma knife radio surgery). These later procedures are very invasive, and most are non-reversible. In both cases, the surgical approach is typically through the nostrils or the greater palatine foramen.

SUMMARY OF THE INVENTION

According to one aspect of the present invention, a surgical guide to facilitate delivery of a therapy delivery device into the pterygopalatine fossa (PPF) of a subject includes a curvilinear body having a distal end portion, a proximal end portion, and an intermediate portion extending between the distal and proximal end portions. The proximal end portion is defined by oppositely disposed first and second surfaces. The proximal end portion and the intermediate portion define a longitudinal plane that extends between the proximal and distal end portions. The distal end portion has an arcuate configuration relative to the longitudinal plane and is defined by oppositely disposed third and fourth surfaces.

According to another aspect of the present invention, a surgical guide to facilitate delivery of a therapy delivery device into the PPF of a subject includes a curvilinear body having a distal end portion, a proximal end portion, and an intermediate portion extending between the distal and proximal end portions. The proximal end portion is defined by oppositely disposed first and second surfaces. The proximal end portion and the intermediate portion define a longitudinal plane that extends between the proximal and distal end portions. The distal end portion has an arcuate configuration relative to the longitudinal plane and is defined by oppositely disposed third and fourth surfaces. The body further includes a groove for receiving the therapy delivery device. The groove extends between the proximal and distal end portions and is embedded in at least a portion of each of the first and third surfaces.

According to yet another aspect of the present invention, a method is provided for treating a medical condition in a subject. One step of the method includes providing a surgical guide. The surgical guide comprises a curvilinear body having a distal end portion, a proximal end portion, and an intermediate portion extending between the distal and proximal end portions. The proximal end portion is defined by oppositely disposed first and second surfaces. The distal end portion is defined by oppositely disposed third and fourth surfaces. The proximal end portion and the intermediate portion define a longitudinal plane that extends between the proximal and distal end portions. The distal end portion has an arcuate configuration relative to the longitudinal plane. The body includes a groove that extends between the proximal and distal end portions and is embedded in at least a portion of each of the first and third surfaces. Next, the distal end portion of the surgical guide is inserted into a gingival-buccal insertion site and advanced until a distal tip of the distal end portion is positioned about the PPF. A therapy delivery device is then mated with the groove of the surgical guide and advanced along the groove to a location on or proximate the SPG. The therapy delivery device is activated to modulate SPG activity.

According to another aspect of the present invention, a method is provided for delivering a neurostimulator to within close proximity of a SPG. One step of the method includes making an incision over a skull and then inserting a surgical guide into the incision. Next, the surgical guide is advanced under a zygomatic bone along a maxillary tuberosity towards a PPF. The neurostimulator is then delivered in close proximity to the SPG.

According to another aspect of the present invention, a surgical guide configured to deliver a neurostimulator into a subject comprises an elongate shaft and a groove on the elongate shaft configured to deploy the neurostimulator. The elongate shaft comprises a contoured distal end portion shaped and configured to be advanced under a zygomatic bone along a maxillary tuberosity towards a PPF.

According to another aspect of the present invention, a method is provided for treating a neurological disorder. One step of the method includes making an incision over a skull and then inserting a surgical guide into the incision. Next, the surgical guide is advanced under a zygomatic bone along a maxillary tuberosity towards a PPF. A neurostimulator is then delivered in close proximity to the SPG, followed by application of an electrical current from the neurostimulator to the SPG to treat the neurological disorder.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 2A is a perspective view showing a surgical guide to facilitate delivery of a therapy delivery device into the PPF of a subject constructed in accordance with another aspect of the present invention;

FIG. 2B is a cross-sectional view of the surgical guide taken along Line 2B-2B in FIG. 2A;

FIG. 2C is a cross-sectional view of the surgical guide taken along Line 2C-2C in FIG. 2A;

FIG. 2D is a cross-sectional view of the surgical guide taken along Line 2D-2D in FIG. 2A;

FIG. 3 is a perspective view showing a surgical guide to facilitate delivery of a therapy delivery device into the PPF of a subject constructed in accordance with another aspect of the present invention;

DETAILED DESCRIPTION

Figure 1:
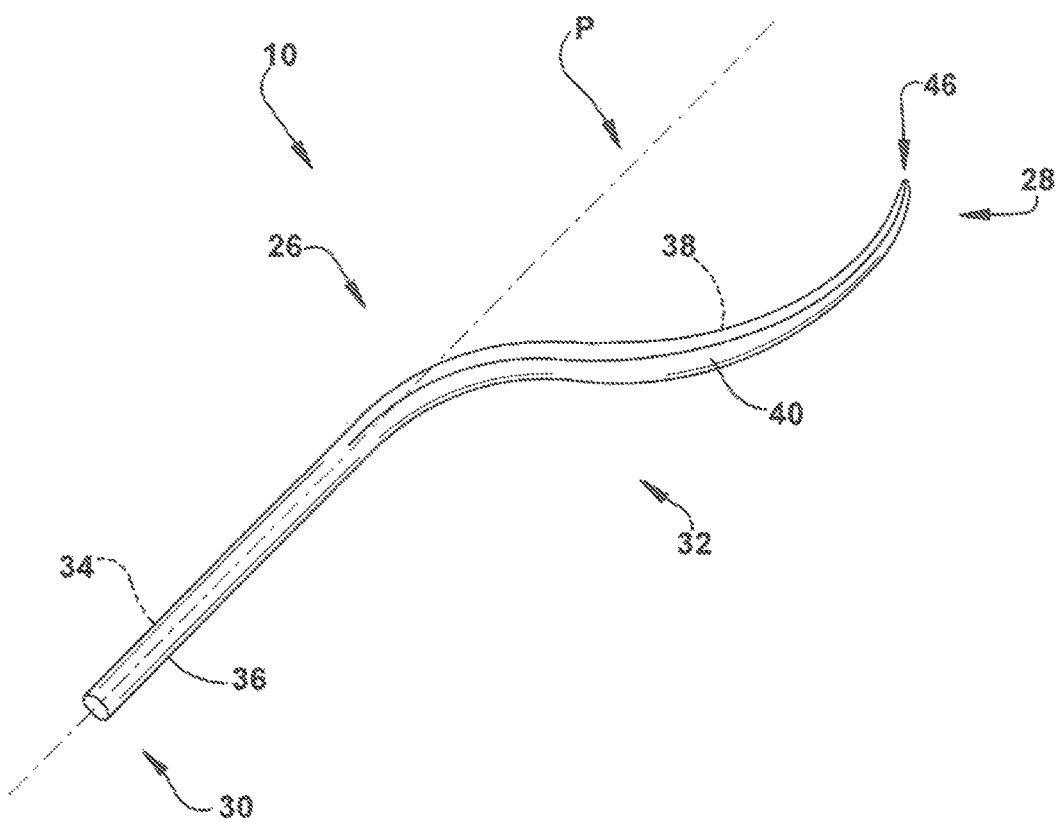
FIG. 1 is a perspective view showing a surgical guide to facilitate delivery of a therapy delivery device into the pterygopalatine fossa (PPF) of a subject constructed in accordance with one aspect of the present invention.
Figure 4:
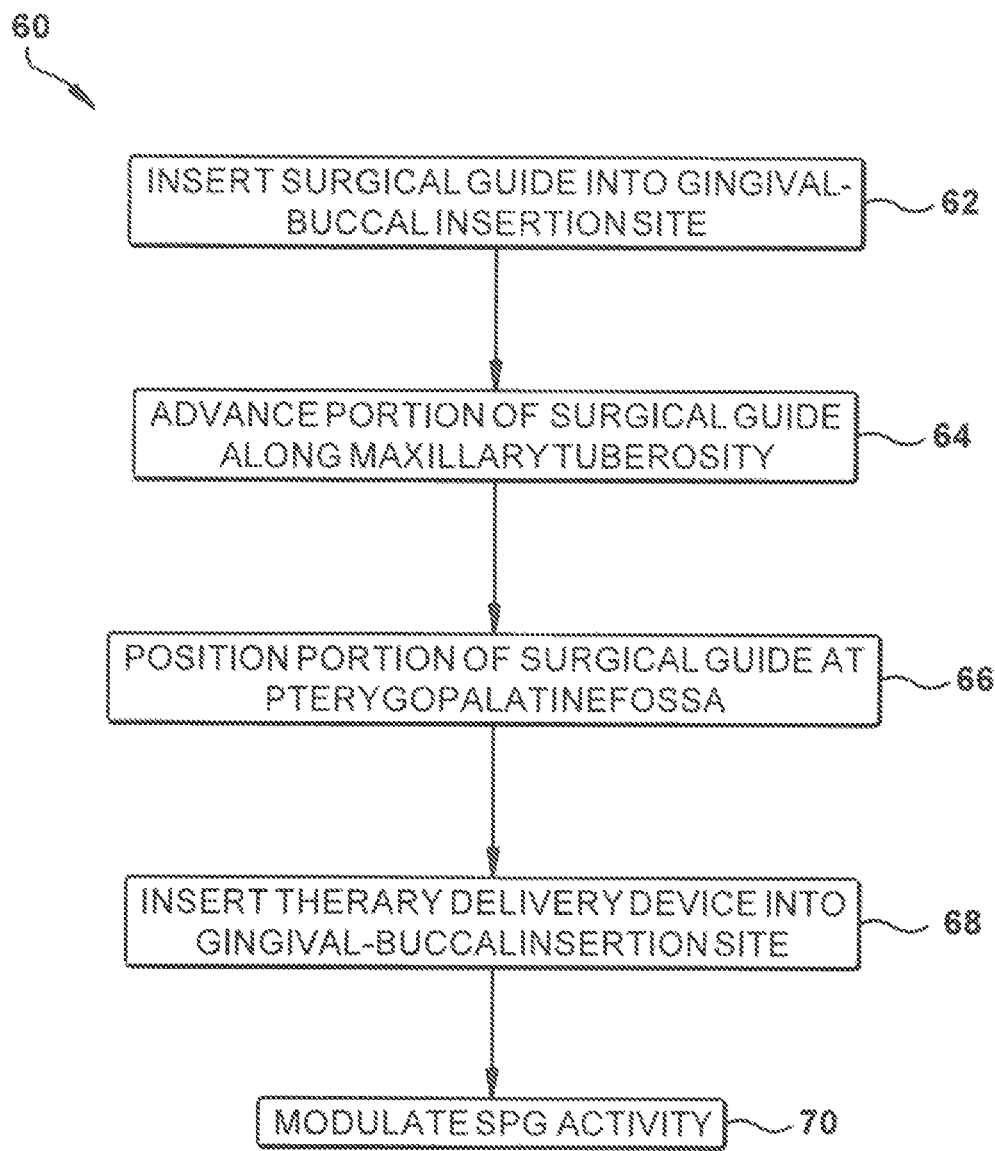
FIG. 4 is a process flow chart illustrating a method for treating a medical condition in a subject according to another aspect of the present invention.

The present invention relates generally to an apparatus and method for delivering therapy delivery devices to craniofacial locations, and more particularly to a surgical guide and method for delivering a therapy delivery device into the pterygopalatine fossa (PPF) of a subject. As representative of one aspect of the present invention, FIGS. 1 and 4 illustrate a surgical guide 10 and related method 60 for facilitating delivery of a therapy delivery device 12 (FIG. 11) into the PPF 14 (FIG. 5) of a subject, respectively. As discussed in greater detail below, it will be appreciated that the present invention may be employed to treat a variety of other chronic or acute medical conditions besides headache and/or facial pain. Examples of such medical conditions can include, but are not limited to, pain, movement disorders, epilepsy, cerebrovascular diseases, autoimmune diseases, sleep disorders, autonomic disorders, urinary bladder disorders, abnormal metabolic states, disorders of the muscular system, and neuropsychiatric disorders.

Unless otherwise defined, all technical terms used herein have the same meaning as commonly understood by one of ordinary skill in the art to which the present invention pertains.

In the context of the present invention, the term "headache" as used herein can refer to migraines, tension headaches, cluster headaches, trigeminal neuralgia, secondary headaches, tension-type headaches, chronic and epsisodic headaches, medication overuse/rebound headaches, chronic paroxysmal hemicrinia headaches, hemicranias continua headaches, post-traumatic headaches, post-herpetic headaches, vascular headaches, reflex sympathetic dystrophy-related headaches, crvicalgia headaches, caroidynia headaches, sciatica headaches, trigeminal headaches, occipital headaches, maxillary headaches, chary headaches, paratrigeminal headaches, petrosal headaches, Sluder's headache, vidian headaches, low CSF pressure headaches, temporomandibular joint (TMJ) headaches, causalgia headaches, myofascial headaches, all primary headaches (e.g., primary stabbing headache, primary cough headache, primary exertional headache, primary headache associated with sexual activity, hypnic headache, and new daily persistent headache), all trigeminal autonomic cephalagias (e.g., episodic paroxysmal hemicranias, SUNCT, all probable TACs, and SUNA), chronic daily headaches, occipital neuralgia, atypical facial pain, neuropathic trigeminal pain, and miscellaneous-type headaches.

As used herein, the term "cluster headache" can refer to extremely painful and debilitating headaches that occur in groups or clusters. Cluster headaches can include cluster-type headaches, histamine headaches, histamine cephalalgia, Raedar's syndrome, and sphenopalatine neuralgia.

As used herein, the term "migraine" can refer to an intense and disabling episodic headache typically characterized by severe pain in one or both sides of the head. Migraines can include, but are not limited to, migraine without aura, migraine with aura, migraine with aura but without headache, menstrual migraines, variant migraines, transformed migraines, complicated migraines, hemiplegic migraines, atypical migraines, chronic migraines, basilar-type migraines, childhood periodic syndromes that are commonly precursors of migraine (e.g., abdominal, cyclic vomiting, BPV, etc.), status migrainous, and all types of probable migraines.

As used herein, the term "facial pain" can refer to direct pain that typically involves nerves supplying the face or, alternatively, indirect (referred) pain from other structures in the head, e.g., blood vessels. The pain may be related to headache (e.g., migraine), muscular syndromes (e.g., TMJ), and herpetic or rheumatic disease or injury.

As used herein, the terms "modulate" or "modulating" can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, biological, magnetic, optical or chemical, or a combination of two or more of these. The terms can also be used to refer to a masking, altering, overriding, or restoring of neuronal activity.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "prevent" shall have its plain and ordinary meaning to one skilled in the art of pharmaceutical or medical sciences. For example, "prevent" can mean to stop or hinder a headache.

As used herein, the terms "treat" or "treating" shall have their plain and ordinary meaning to one skilled in the art of pharmaceutical or medical sciences. For example, "treat" or "treating" can mean to prevent or reduce a headache.

As used herein, the term "medical condition" can refer to pain, movement disorders, epilepsy, cerebrovascular diseases, autoimmune diseases, sleep disorders, autonomic disorders, urinary bladder disorders, abnormal metabolic states, disorders of the muscular system, infectious and parasitic diseases (as provided in ICD-9 codes 1-139), neoplasms (as provided in ICD-9 codes 140-239), endocrine diseases, nutritional and metabolic diseases, immunological diseases (as provided in ICD-9 codes 240-279), diseases of the blood and blood-forming organs (as provided in ICD-9 codes 280-289), mental disorders (as provided in ICD-9 codes 290-319), diseases of the nervous system (as provided in ICD-9 codes 320-359), diseases of the sense organs (as provided in ICD-9 codes 360-389), diseases of the circulatory system (as provided in ICD-9 codes 390-459), diseases of the respiratory system (as provided in ICD-9 codes 460-519), diseases of the digestive system (as provided in ICD-9 codes 520-579), diseases of the genitourinary system (as provided in ICD-9 codes 580-629), diseases of the skin and subcutaneous tissue (as provided in ICD-9 codes 680-709), diseases of the musculoskeletal system and connective tissue (as provided in ICD-9 codes 710-739), congenital anomalies (as provided in ICD-9 codes 740-759), certain conditions originating in the perinatal period (as provided in ICD-9 codes 760-779), and symptoms, signs, and ill-defined conditions (as provided in ICD-9 codes 780-799).

Pain treatable by the present invention can be caused by conditions including, but not limited to, migraine headaches, including migraine headaches with aura, migraine headaches without aura, menstrual migraines, migraine variants, atypical migraines, complicated migraines, hemiplegic migraines, transformed migraines, and chronic daily migraines, episodic tension headaches, chronic tension headaches, analgesic rebound headaches, episodic cluster headaches, chronic cluster headaches, cluster variants, chronic paroxysmal hemicranias, hemicrania continua, post-traumatic headache, post-traumatic neck pain, post-herpetic neuralgia involving the head or face, pain from spine fracture secondary to osteoporosis, arthritis pain in the spine, headache related to cerebrovascular disease and stroke, headache due to vascular disorder, reflex sympathetic dystrophy, cervicalgia (which may be due to various causes, including, but not limited to, muscular, discogenic, or degenerative, including arthritic, posturally related, or metastatic), glossodynia, carotidynia, cricoidynia, otalgia due to middle ear lesion, gastric pain, sciatica, maxillary neuralgia, laryngeal pain, myalgia of neck muscles, trigeminal neuralgia (sometimes also termed tic douloureux), post-lumbar puncture headache, low cerebro-spinal fluid pressure headache, TMJ joint disorder, atypical facial pain, ciliary neuralgia, paratrigeminal neuralgia (sometimes also termed Raeder's syndrome); petrosal neuralgia, Eagle's syndrome, idiopathic intracranial hypertension, orofacial pain, myofascial pain syndrome involving the head, neck, and shoulder, chronic migraneous neuralgia, cervical headache, paratrigeminal paralysis, SPG neuralgia (sometimes also termed lower-half headache, lower facial neuralgia syndrome, Sluder's neuralgia, and Sluder's syndrome), carotidynia, vidian neuralgia, causalgia, and/or a combination of the above.

Movement disorders treatable by the present invention may be caused by conditions including, but not limited to, Parkinson's disease, cerebropalsy, dystonia, essential tremor, and hemifacial spasms.

Epilepsy treatable by the present invention may be, for example, generalized or partial.

Cerebrovascular disease treatable by the present invention may be caused by conditions including, but not limited to, aneurysms, strokes, and cerebral hemorrhage.

Autoimmune diseases treatable by the present invention include, but are not limited to, multiple sclerosis.

Sleep disorders treatable by the present invention may be caused by conditions including, but not limited to, sleep apnea and parasomnias.

Autonomic disorders treatable by the present invention may be caused by conditions including, but not limited to, gastrointestinal disorders, including but not limited to gastrointestinal motility disorders, nausea, vomiting, diarrhea, chronic hiccups, gastroesphageal reflux disease, and hypersecretion of gastric acid, autonomic insufficiency; excessive epiphoresis, excessive rhinorrhea; and cardiovascular disorders including, but not limited, to cardiac dysrythmias and arrythmias, hypertension, and carotid sinus disease.

Urinary bladder disorders treatable by the present invention may be caused by conditions including, but not limited to, spastic or flaccid bladder.

Abnormal metabolic states treatable by the present invention may be caused by conditions including, but not limited to, hyperthyroidism or hypothyroidism.

Disorders of the muscular system treatable by the present invention can include, but are not limited to, muscular dystrophy, and spasms of the upper respiratory tract and face.

Neuropsychiatric or mental disorders treatable by the present invention may be caused by conditions including, but not limited to, depression, schizophrenia, bipolar disorder, and obsessive-compulsive disorder.

A brief discussion of the pertinent anatomy and neurophysiology is provided to assist the reader with understanding the present invention. The autonomic nervous system, which innervates numerous pathways within the human body and consists of two divisions: the sympathetic and the parasympathetic nervous systems. The sympathetic and parasympathetic nervous systems are antagonistic in their action, balancing the other system's effects within the body. The sympathetic nervous system (SNS) usually initiates activity within the body, preparing the body for action, while the parasympathetic nervous system (PNS) primarily counteracts the effects of the SNS.

Figure 5:
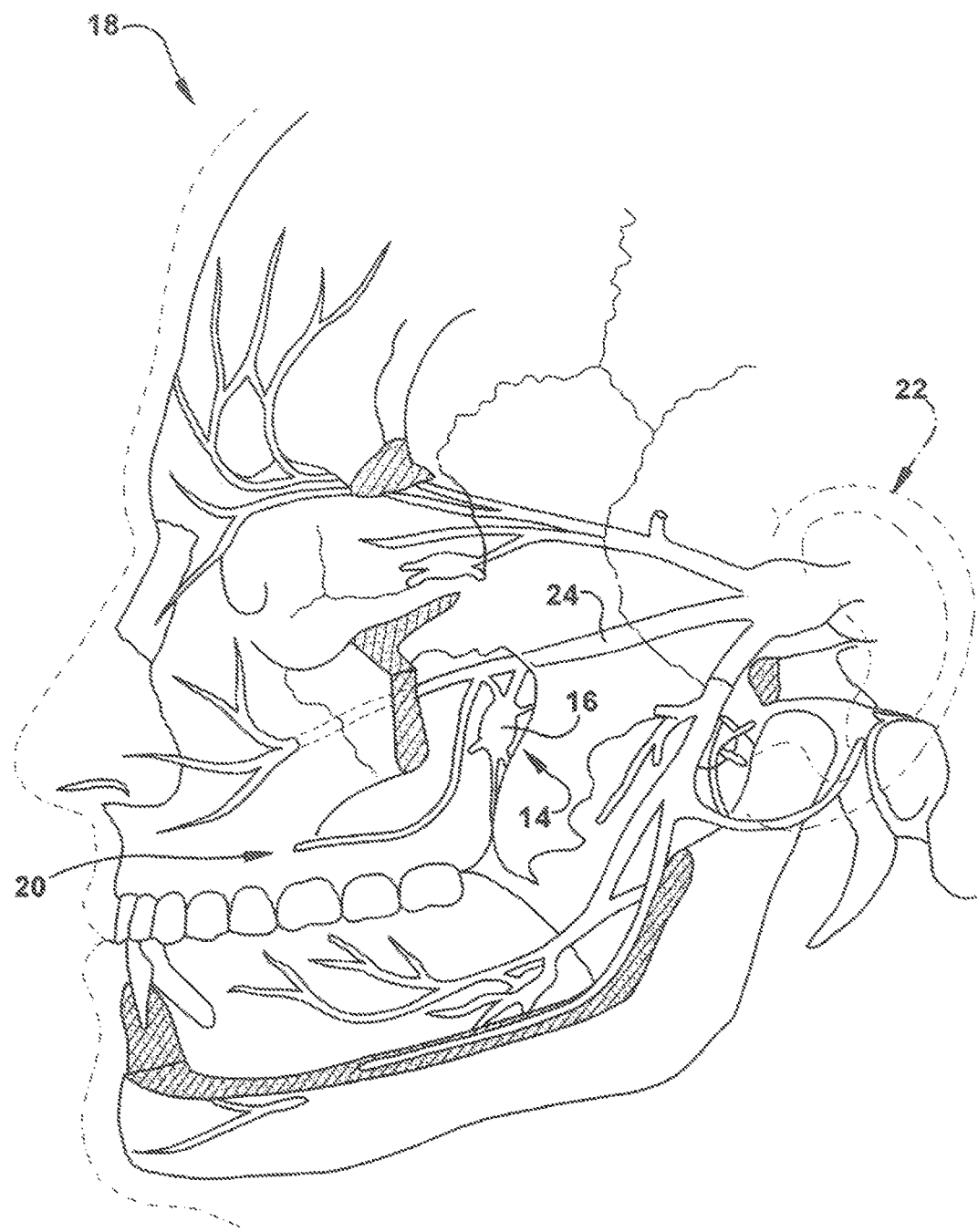
FIG. 5 is a perspective view showing the nervous innervation of the anterior craniofacial skeleton.

The sphenopalatine ganglia 16 are located on both sides of the head 18 (FIG. 5). It shall be assumed for the following discussion of the present invention that reference is being made to the sphenopalatine ganglion 16 (SPG) located on the left side of the head 18. The SPG 16 is located behind the maxilla 20 in the PPF 14, posterior to the middle nasal turbinate (not shown in detail). The SPG 16 is part of the parasympathetic division of the autonomic nervous system; however, the SPG 16 has both sympathetic and parasympathetic nerve fibers, as well as sensory and motor nerve fibers either synapsing within the ganglion (e.g., parasympathetic) or fibers that are passing through the ganglion and not synapsing (e.g., sympathetic, sensory, and motor).

The parasympathetic activity of the SPG 16 is mediated through the greater petrosal nerve (not shown), while the sympathetic activity of the SPG is mediated through the deep petrosal nerve (not shown), which is essentially an extension of the cervical sympathetic chain (not shown). Sensory sensations generated by or transmitted through the SPG 16 include, but are not limited to, sensations to the upper teeth, feelings of foreign bodies in the throat, and persistent itching of the ear 22. The SPG 16 transmits sensory information, including pain, to the trigeminal system via the maxillary division 24 and ophthalmic division (not shown).

One aspect of the present invention is illustrated in FIG. 1 and comprises a surgical guide 10 to facilitate delivery of a therapy delivery device 12 (FIG. 11) into the PPF 14 (FIG. 5) of a subject. As shown in FIG. 1, the surgical guide 10 includes a curvilinear body 26 or elongate shaft having a contoured distal end portion 28, a proximal end portion 30, and an intermediate portion 32 extending between the distal and proximal end portions. The proximal end portion 30 and the distal end portion 28 define a longitudinal plane P that extends between the proximal and distal end portions. The surgical guide 10 can be made of a rigid or semi-rigid medical grade metal or metal alloy, such as stainless steel, medical grade plastics, polymers, and the like. As described in more detail below, the curvilinear configuration of the surgical guide 10 is shaped and configured for simply and accurately traversing the anterior craniofacial skeletal anatomy to reach the PPF 14 (FIG. 5).

The proximal end portion 30 (FIG. 1) includes oppositely disposed first and second surfaces 34 and 36 and has a suitable cross-sectional shape to facilitate handling of the surgical guide 10 during surgical procedures. As shown in FIG. 1, for example, the proximal end portion 30 has a rounded, cross-sectional shape that tapers at about the intermediate portion 32 into oppositely disposed third and fourth surfaces 38 and 40. It will be appreciated that the proximal end portion 30 can have any suitable cross-sectional shape (e.g., flattened, elliptical, etc.).

The distal end portion 28 has an arcuate configuration relative to the longitudinal plane P and is defined by the third and fourth surfaces 38 and 40. The third surface 38 has a flattened cross-sectional shape and is adapted, shaped, and configured to traverse under the zygomatic bone 42 (FIG. 6) along the maxillary tuberosity 44 until a distal tip 46 of the distal end portion 28 (FIG. 1) is positioned just within or within the PPF 14 (FIG. 3). Although the fourth surface 40 (FIG. 1) is also shown as having a flattened cross-sectional shape, it will be appreciated that the fourth surface can have other cross-sectional shapes as well (e.g., elliptical).

Illustrated in FIGS. 2A-D is another aspect of the present invention comprising a surgical guide $10_a$ for guiding a therapy delivery device 12 (FIG. 11) to the PPF 14 of a subject. In FIGS. 2A-D, structures that are identical as structures in FIG. 1 use the same reference numbers, whereas structures that are similar but not identical carry the suffix "a".

As shown in FIGS. 2A-B, the surgical guide $10_a$ can include a curvilinear body $26_a$ or elongated shaft having a contoured distal end portion $28_a$, a proximal end portion $30_a$, and an intermediate portion $32_a$ extending between the distal and proximal end portions. The proximal end portion $30_a$ and the distal end portion $28_a$ can define a longitudinal plane P that extends between the proximal and distal end portions. The surgical guide $10_a$ can be made of a rigid or semi-rigid medical grade metal or metal alloy, such as stainless steel, medical grade plastics, polymers, and the like. As described in more detail below, the curvilinear configuration of the surgical guide $10_a$ provides a means for simply and accurately traversing the anterior craniofacial skeletal anatomy to reach the PPF 14 (FIG. 5).

The proximal end portion $30_a$ (FIGS. 2A-B) can include oppositely disposed first and second surfaces $34_a$ and 36 and have a suitable cross-sectional shape to facilitate handling of the surgical guide $10_a$ during surgical procedures. As shown in FIGS. 2A-B, for example, the proximal end portion $30_a$ can have a rounded, cross-sectional shape that tapers at about the intermediate portion $32_a$ into oppositely disposed third and fourth surfaces $38_a$ and 40. It will be appreciated that the proximal end portion 30 can have any suitable cross-sectional shape (e.g., flattened, elliptical, etc.).

The distal end portion $28_a$ can have an arcuate configuration relative to the longitudinal plane P and be defined by the third and fourth surfaces $38_a$ and 40. The third surface $38_a$ can have a flattened cross-sectional shape and be adapted, shaped, and configured to traverse under the zygomatic bone 42 (FIG. 6) along the maxillary tuberosity 44 until a distal tip 46 (FIGS. 2A-B) of the distal end portion $28_a$ is positioned about the PPF 14 (FIG. 5). Although the fourth surface 40 (FIGS. 2A-B) is also shown as having a flattened cross-sectional shape, it will be appreciated that the fourth surface can have other cross-sectional shapes as well (e.g., elliptical).

The surgical guide $10_a$ can additionally include a groove 48 adapted to receive a therapy delivery device 12 (FIG. 11) and facilitate precise, directional placement of the therapy delivery device about the PPF 14. The groove 48 can extend between the proximal and distal end portions $30_a$ and $28_a$ and be embedded or recessed in at least a portion of each of the first and third surfaces $34_a$ and $38_a$. As shown in FIG. 2A, the groove 48 can extend between a proximal tip 50 of the proximal end portion $30_a$ and the distal end portion $28_a$. The particular dimensions of the groove 48 will vary depending upon the size of surgical guide $10_a$. In one example of the present invention, the groove 48 can have a depth of between about 0.5 mm and 1.2 mm, a width of between about 1 mm and 1.5 mm, and a length of between about 2 cm and 8 cm.

Figure 11:
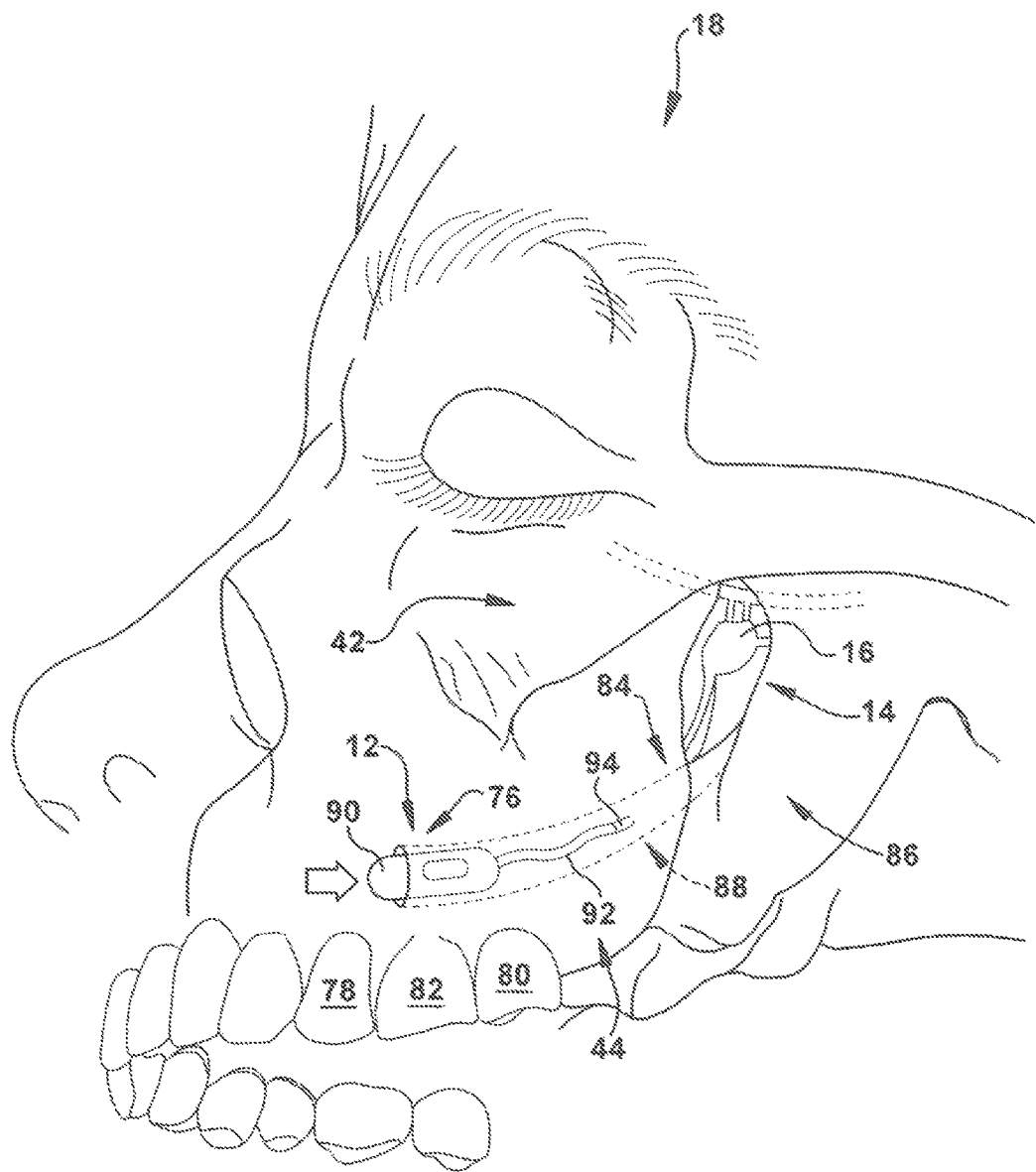
FIG. 11 is a perspective view showing a therapy delivery device being inserted through the gingival-buccal insertion site (indicated by arrow) and into the tunnel or trough in FIG. 10.

The depth and width of the groove 48 can vary across the length of the surgical guide $10_a$ to facilitate engagement and release of the therapy delivery device 12 (FIG. 11). For example, a portion of the groove 48 (FIG. 2B) located at the proximal tip 50 can have a first depth $D_1$ that is greater than a second depth $D_2$ (FIG. 2C) located at the distal end portion $28_a$. The varying depth of the groove 48 can form a gradual taper that extends between the proximal and distal end portions $30_a$ and $28_a$. As described in more detail below, the varying depth of the groove 48 facilitates engagement of the therapy delivery device 12 (FIG. 11) at the proximal end portion $30_a$ (FIG. 2A) while also promoting disengagement of the therapy delivery device (FIG. 11) from the distal end portion $28_a$ (FIG. 2A) as the therapy delivery device is advanced toward the distal tip 46. Although the groove 48 is shown in FIGS. 2A-C as having a semi-circular cross-sectional shape, it will be appreciated that the groove can have other cross-sectional shapes (e.g., square-shaped, V-shaped, etc.) to facilitate engagement of the therapy delivery device 12 (FIG. 11) with the groove.

Illustrated in FIG. 3 is another aspect of the present invention comprising a surgical guide $10_b$ for guiding a therapy delivery device 12 (FIG. 11) to the PPF 14 of a subject. In FIG. 3, structures that are identical as structures in FIG. 1 use the same reference numbers, whereas structures that are similar but not identical carry the suffix "b".

As shown in FIG. 3, the surgical guide $10_b$ can include a curvilinear body $26_b$ or elongated shaft having a contoured distal end portion $28_b$, a proximal end portion 30, and an intermediate portion $32_b$ extending between the distal and proximal end portions. The proximal end portion 30 and the distal end portion $28_b$ can define a longitudinal plane P that extends between the proximal and distal end portions. The surgical guide $10_b$ can be made of a rigid or semi-rigid medical grade metal or metal alloy, such as stainless steel, medical grade plastics, polymers, and the like. As described in more detail below, the curvilinear configuration of the surgical guide $10_b$ provides a means for simply and accurately traversing the anterior craniofacial skeletal anatomy to reach the PPF 14 (FIG. 5).

The proximal end portion 30 (FIG. 3) can include oppositely disposed first and second surfaces 34 and 36 and a suitable cross-sectional shape to facilitate handling of the surgical guide $10_b$ during surgical procedures. As shown in FIG. 3, for example, the proximal end portion 30 can have a rounded, cross-sectional shape that tapers at about the intermediate portion $32_b$ into oppositely disposed third and fourth surfaces $38_b$ and 40. It will be appreciated that the proximal end portion 30 can have any suitable cross-sectional shape (e.g., flattened, elliptical, etc.).

The distal end portion $28_b$ can have an arcuate configuration relative to the longitudinal plane P and be defined by the third and fourth surfaces $38_b$ and 40. The third surface $38_b$ can have a flattened cross-sectional shape and be adapted, shaped, and configured to traverse under the zygomatic bone 42 (FIG. 6) along the maxillary tuberosity 44 until a distal tip 46 (FIG. 3) of the surgical guide $10_b$ is positioned about the PPF 14 (FIG. 5). Although the fourth surface 40 (FIG. 3) is also shown as having a flattened cross-sectional shape, it will be appreciated that the fourth surface can have other cross-sectional shapes as well (e.g., elliptical).

The surgical guide $10_b$ can additionally comprise a trough member 72 for receiving a therapeutic delivery device 12 (FIG. 11). The trough member 72 (FIG. 3) can have a curved configuration and be slidably connected to the third surface $38_b$ via a rail mechanism 74 (not shown in detail). The trough member 72 can have a rigid, semi-rigid, or flexible configuration and be made of any appropriate medical grade material. The rail mechanism 74 can comprise a recessed channel (not shown in detail) that extends along a portion of the third surface $38_b$ between the intermediate portion $32_b$ and the distal tip 46 of the surgical guide $10_b$. Additionally, the trough member 72 can include an interlocking member (not shown) that is slidably receivable within the recessed channel. As described in more detail below, the trough member 72 can slide across the third surface $38_b$ to facilitate delivery of a therapeutic delivery device 12 (FIG. 11) to the PPF 14.

FIG. 4 is a process flow diagram illustrating another aspect of the present invention. In FIG. 4, a method 60 is provided for treating a medical condition (e.g., headache) in a subject using the surgical guide 10 illustrated in FIG. 1. At Step 62 of the method 60, the surgical guide 10 is inserted into a gingival-buccal insertion site 76. Prior to inserting the surgical guide 10, however, the neuroanatomy of the subject is determined using one or more imaging techniques (e.g., MRI, CT, ultrasound, X-ray, fluoroscopy, or combinations thereof). In particular, the anatomy of the subject's skull, including the location and size of the PPF 14 can be determined prior to implantation of a therapy delivery device 12.

Figure 6:
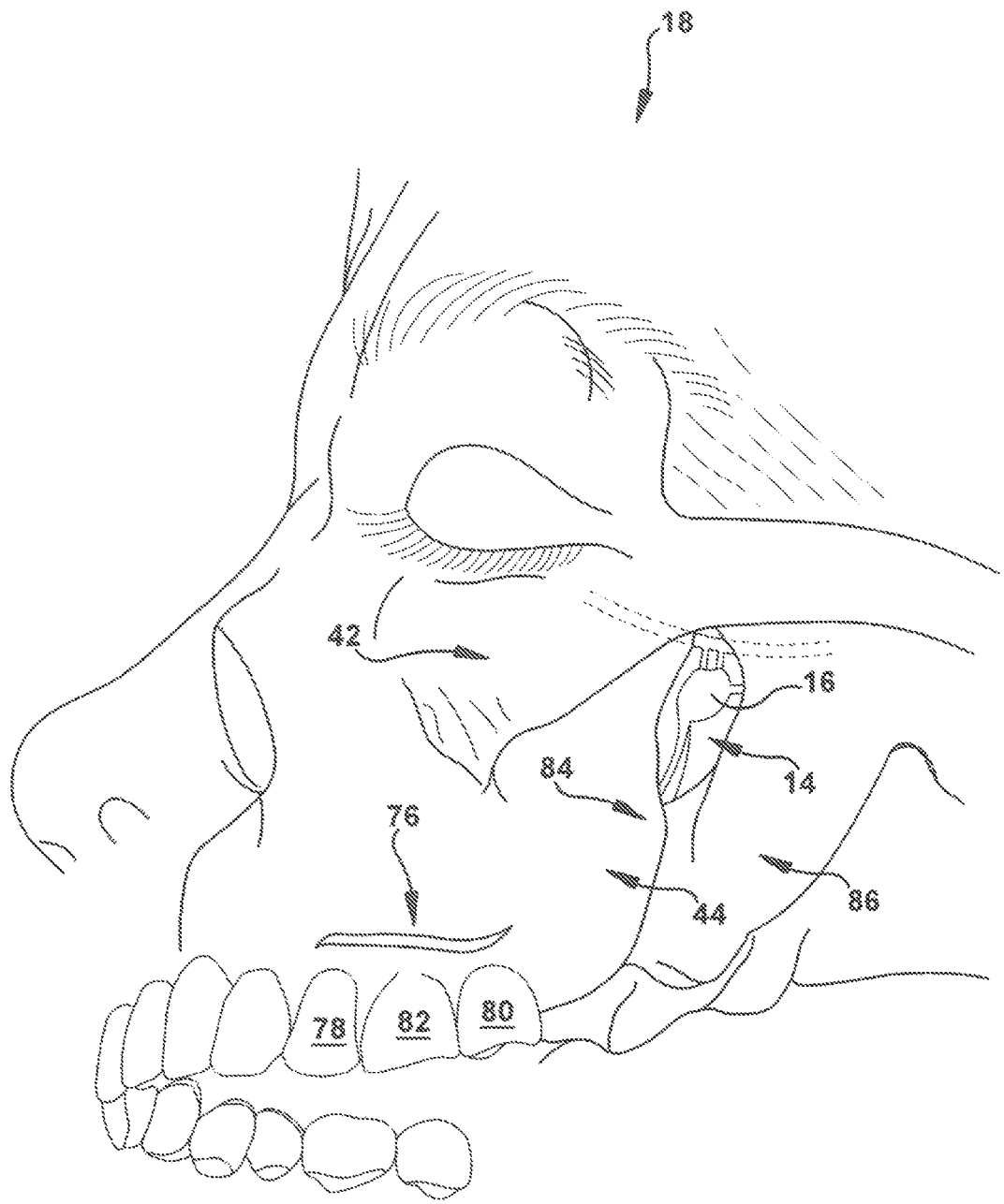
FIG. 6 is a perspective view of the anterior craniofacial skeleton showing a gingival-buccal insertion site.
Figure 7:
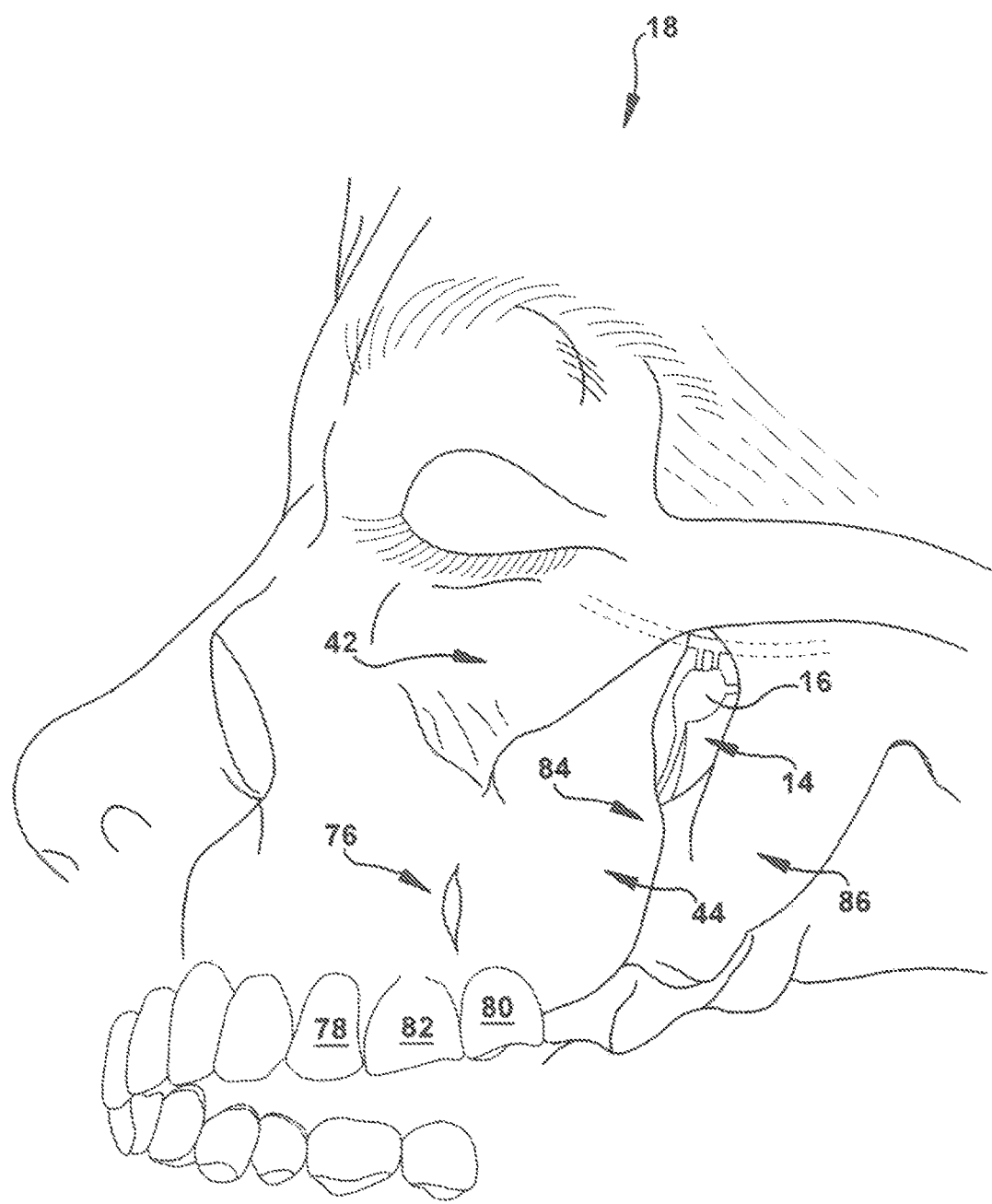
FIG. 7 is a perspective view of the anterior craniofacial skeleton showing an alternative configuration of the gingival-buccal insertion site in FIG. 6.

After assessing the neuroanatomy of the subject, the implant procedure begins by creating the gingival-buccal insertion site 76. As shown in FIG. 6, the gingival-buccal insertion site 76 includes an incision made in the gingival tissue substantially in between, and superior to, the first and third molars 78 and 80. For example, a #10 scalpel blade (not shown) can be used to make an incision of about 0.5 cm to about 1.5 cm that extends between the first 78, second 82, and/or third 80 molars and is substantially parallel to the gum line (e.g., about 3-5 mm superior to the mucogingival junction). It should be appreciated that the gingival-buccal insertion site 76 can be made at other locations and have a different geometry than the incision shown in FIG. 6. For example, the gingival-buccal insertion site 76 can comprise a substantially incision (e.g., about 0.5 cm to about 1.5 cm in length) made in a superior-inferior manner between the second and third molars 82 and 80 (FIG. 7).

Figure 8:
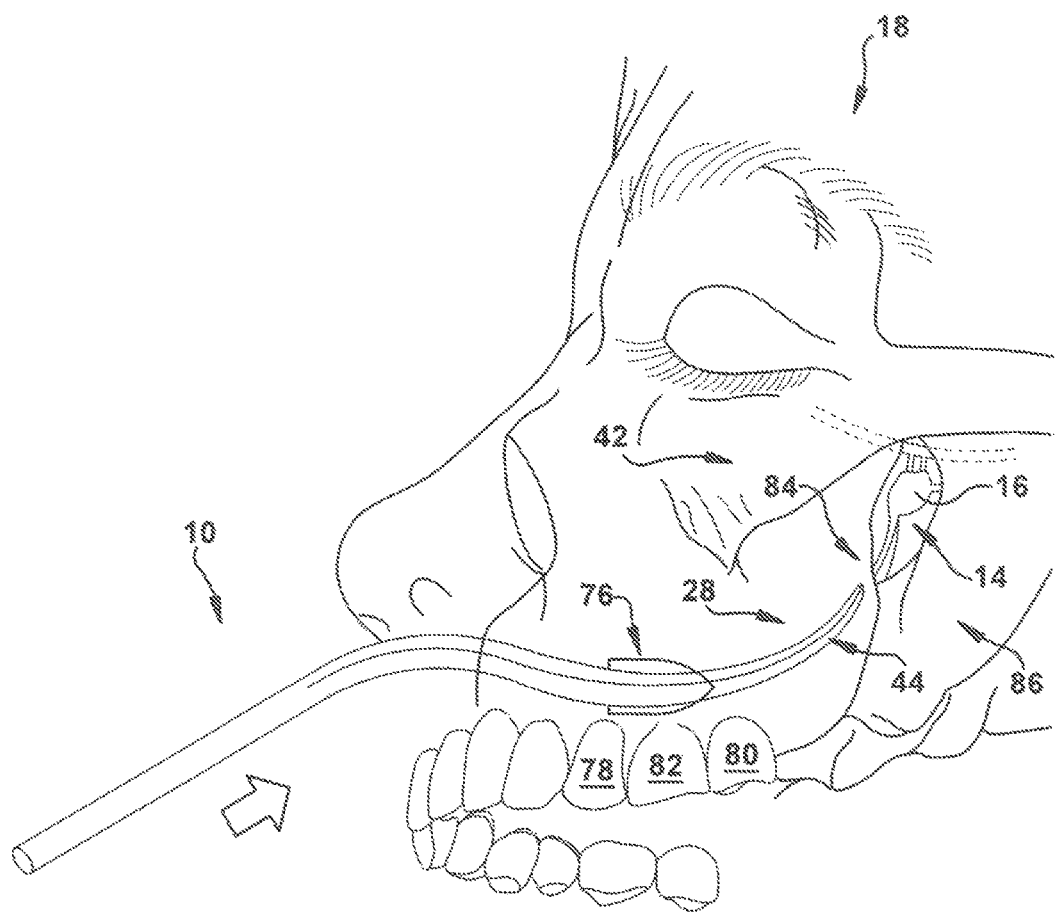
FIG. 8 is a perspective view showing a surgical guide (FIG. 1) being inserted into the gingival-buccal insertion site of FIG. 6.
Figure 9:
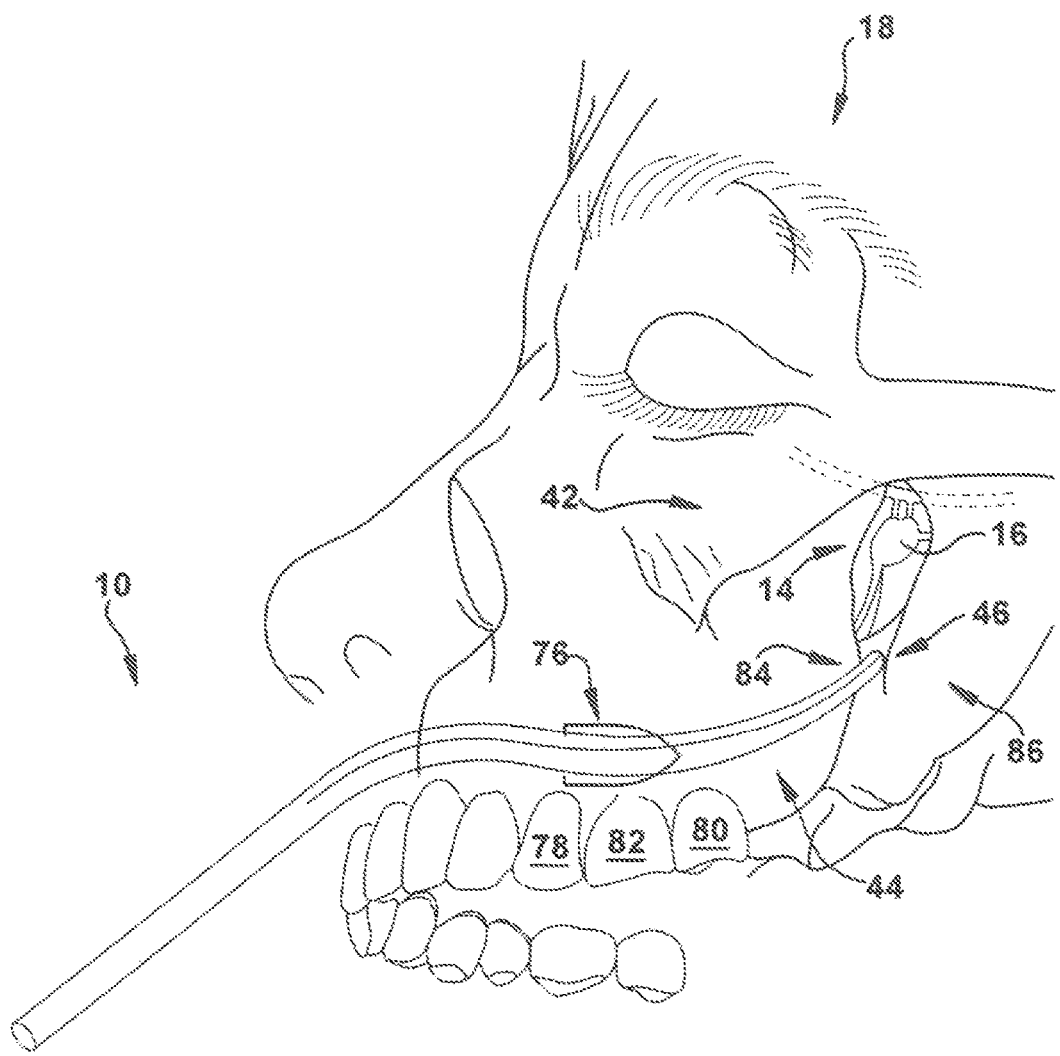
FIG. 9 is a perspective view showing a distal end portion of the surgical guide in FIG. 8 engaging the junction formed by the posterior maxillary buttress and the pterygoid plate.

As noted above, the distal end portion 28 of the surgical guide 10 is inserted into the gingival-buccal insertion site 76 at Step 62. As shown in FIG. 8, the surgical guide 10 is urged in a posterior direction (indicated by arrow) so that the third surface 38 of the distal end portion 28 traverses under the zygomatic bone 42 along the maxillary tuberosity 44 (Step 64). The surgical guide 10 is then advanced further until the distal tip 46 engages the junction formed by the posterior maxillary buttress 84 and the pterygoid plate 86, just inferior to the PPF 14 (FIG. 9). Advancement of the surgical guide 10 may naturally stop when the distal tip 46 is correctly positioned at the junction formed by the posterior maxillary buttress 84 and the pterygoid plate 86.

At this point, the surgical guide 10 is rotated in a superior direction until the distal tip 46 is within the PPF 14. This can be done by carefully "walking" the distal tip 46 up the pterygoid plate 86 until the distal tip (or other desired portion of the distal end portion 28) slides into the PPF 14 (Step 66). Advantageously, use of the surgical guide 10 to access the PPF 14 provides additional safety to the method

Figure 10:
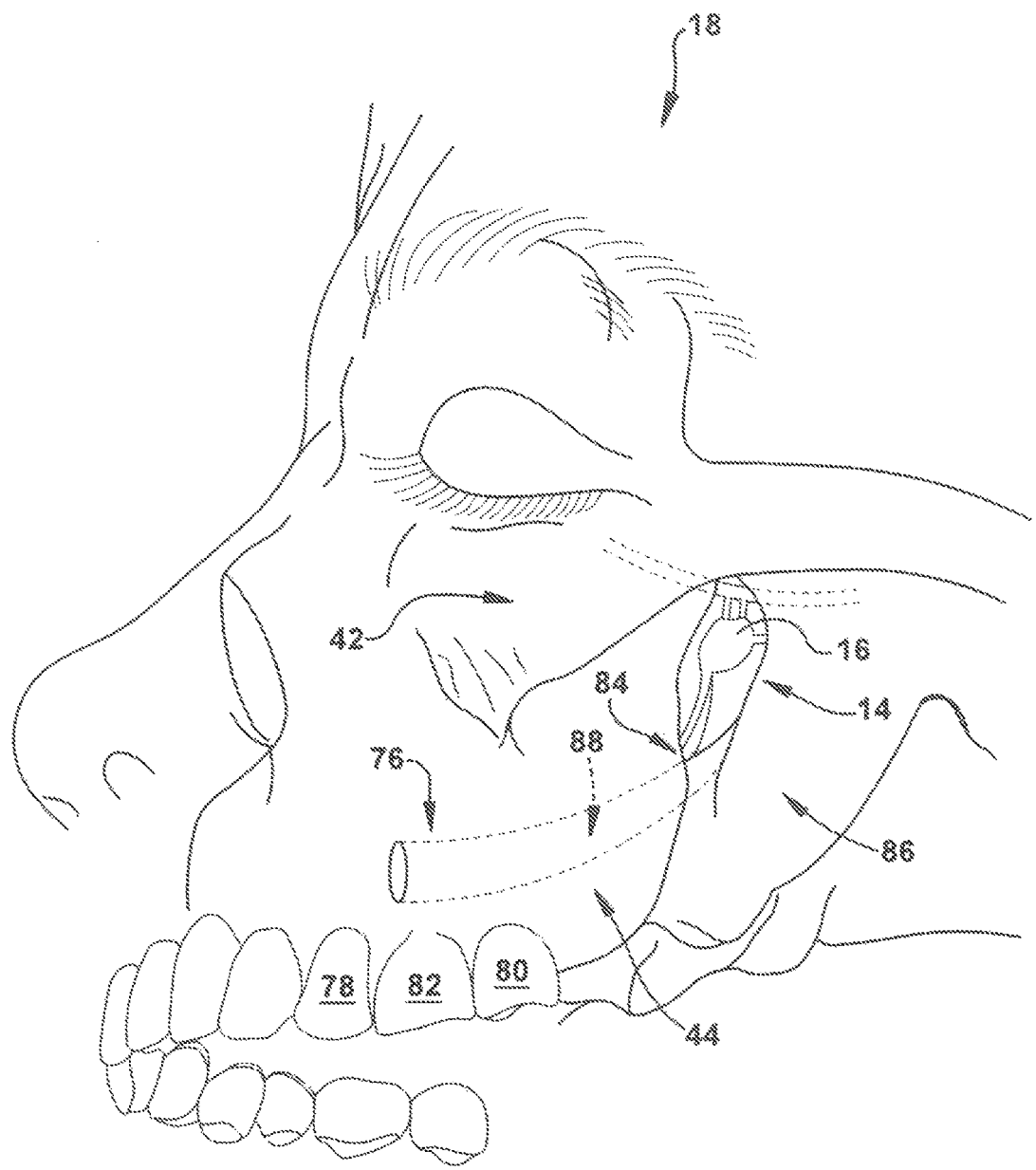
FIG. 10 is a perspective view showing a tunnel or trough (indicated by dashed lines) formed upon removal of the surgical guide in FIG. 9.

60 by reducing the risk of complications associated with the orbit and/or nasal cavities. After the distal tip 46 is appropriately positioned, the surgical guide 10 is removed from the subject to expose a tunnel 88 (FIG. 10) that extends between the gingival-buccal insertion site 76 and the PPF 14.

Figure 12:
FIG. 12 is a perspective view showing the therapy delivery device in FIG. 11 implanted in a subject.

At Step 68, a therapy delivery device 12 is inserted into the gingival-buccal insertion site 76 after removal of the surgical guide 10 (FIG. 11). The therapy delivery device 12 can include any medical device or apparatus capable of delivering a therapy signal (e.g., an electrical signal and/or a chemical agent) to a target site (e.g., the SPG 16). FIGS. 11-12 illustrate one example of a therapy delivery device 12 comprising an implantable neurostimulator. The neurostimulator can include a controller 90 operably connected to an electrical lead 92 that includes at least one electrode 94. It will be appreciated that the therapy delivery device 12 can also include temporary or short-term devices, such as electrical leads or catheters.

The electrode(s) 94 comprising the neurostimulator can be monopolar, bipolar, or multipolar, and can operate as a cathode or an anode. The electrode(s) 94 can be comprised of one or more electrically conductive materials, such as activated iridium, rhodium, titanium, platinum, or a combination thereof. All or only a portion of the electrode(s) 94 may be coated with a thin surface layer of iridium oxide, titanium nitride, or other surface modifications to enhance electrical sensitivity.

The electrical lead 92 can comprise carbon, doped silicon, or silicon nitride. The electrical lead 92 can also be provided with a biocompatible fabric collar or band (not shown) about the periphery of the electrode(s) 94 to allow the electrical lead to be more readily sutured or glued into place. Additionally, the controller 90 can include a fixation plate (e.g., made of titanium) (not shown) that uses standard anterior craniofacial screws to permit attachment of the neurostimulator to a bony structure (or structures) surrounding the PPF 14. The controller 90 can be used to operate and/or supply power to the electrode(s) 94.

The controller 90 may be powered by a battery (not shown) (which can be rechargable), an external power supply, a fuel cell, a battery pack for external use, or via biological energy harvesting. Where the therapeutic delivery device 12 comprises a stimulation lead, the controller 90 may change power output to the electrode(s) 94 by way of polarity, pulse width, amplitude, frequency, voltage, current, and/or waveform. Where the therapeutic delivery device 12 comprises a drug port, the controller 90 may change its output such that a pump, pressure source, or proportionally controlled orifice increases or decreases the rate at which a therapeutic agent is delivered to a target site (e.g., the SPG 16).

The controller 90 may operate any number or combination of electrodes 94 and/or therapeutic agent delivery devices. For example, the controller 90 may be connected to stimulation leads and a peristaltic pump for delivering a therapeutic agent to a target site (e.g., the SPG 16) near the electrode(s) 94. The controller 90 may be entirely implanted within the subject or, alternatively, positioned externally about the subject (e.g., by leads).

Where the controller 90 enables delivery of an electrical signal to a target site (e.g., the SPG 16), the electrical signal may be episodic, continuous, phasic, in clusters, intermittent, upon demand by the subject or medical personnel, or pre-programmed to respond to a sensor (not shown) (e.g., a closed-loop system). The electrical signal can be operated at a constant voltage (e.g., at about 0.1 v to about 25 v), at a constant current (e.g., at about 0.1 microampes to about 5 milliamps), at a constant frequency (e.g., at about 1 Hz to about 200 Hz), and at a constant pulse-width (e.g., at about 10 μsec to about 2,000 μsec). Application of the electrical signal can be monopolar, bipolar, or multipolar, depending upon the polarity of the electrode(s) 94. The waveform may be, for example, biphasic, square wave, sine wave, or other electrically safe and feasible combinations.

Where the controller 90 enables delivery of a therapeutic agent to a target site (e.g., the SPG 16), the therapeutic agent may be delivered to the target site prior to, concurrent with, subsequent to, or instead of electrical neuromodulation. The therapeutic agent may be a neurotransmitter mimetic, neuropeptide, hormone, pro-hormone, antagonist, agonist, reuptake inhibitor or degrading enzyme thereof, peptide, protein, chemical agent, amino acid, nucleic acid, stem cell, or any combination thereof, and may be delivered by a slow release matrix or drug pump. Delivery of the therapeutic agent may be continuous, intermittent, chronic, phasic or episodic.

Referring again to FIG. 11, the therapy delivery device 12 is advanced into the gingival-buccal insertion site 76 (indicated by arrow) and through the tunnel 88 until the electrode(s) 94 is/are positioned within the PPF 14 (Step 68). The position of the therapy delivery device 12 can then be adjusted, if needed, so that the electrode(s) 94 is/are situated on or proximate to all or only a portion of the target site (i.e., the SPG 16) (FIG. 12). If it has not already been done, the electrode(s) 94 and the controller 90 can be anchored securely at the site of implantation so that the electrical signal delivered by the electrode(s) will consistently modulate the same region(s) of the SPG 16.

As the exact parameters of effective SPG 16 neuromodulation may vary between subjects, the therapy delivery device 12 may be controllable so that the electrical signal can be remotely adjusted to desired settings, and retrieval of the therapy delivery device from the subject is not necessary to adjust the subject's therapy. Remote control of the electrical signal can be affected, for example, using either conventional telemetry with an implanted pulse generator (not shown) or, alternatively, using an implanted radiofrequency receiver (not shown) coupled to an external transmitter (not shown). It should be understood that as related technologies advance, other modalities for remote control of therapy delivery devices 12 may be employed to adjust and modulate the parameters of electric current delivery.

At Step 70 of the method 60, an electrical signal is delivered to the electrode(s) 94 (or a combination of the electrodes, where applicable) so that the electrical signal is directly applied to the SPG 16. Delivery of the electrical signal to the SPG 16 modulates SPG activity, which leads to pain intensity reduction. As unregulated and increased nerve transmission is essential for the body to propagate and recognize pain, modulating nerve impulse transmissions through the SPG 16 can diminish the pain experienced by the subject. Upon delivery of the electrical signal to the electrode(s) 94, the subject may be asked to report any sensation, such as pain or paresthesia. The position of the electrical lead 92 or frequency of electrical energy being delivered to the electrode(s) 94 may then be adjusted until the subject reports that the stimulation is comfortable or has caused a substantial reduction in pain intensity. After successful implantation of the therapy delivery device 12, the subject (or a medical professional) can alter the electrical signal at the earliest onset of pain.

It should be appreciated that the therapy delivery device 12 can be part of an open- or closed-loop system. In an open-loop system, for example, a physician or subject may, at any time, manually or by the use of pumps, motorized elements, etc., tailor treatment parameters, such as pulse amplitude, pulse-width, pulse frequency, electrode selections, or duty cycle. Alternatively, in a closed-loop system, electrical parameters may be automatically tailored in response to a sensed symptom or a related symptom indicative of a headache or other medical condition(s). In a closed-loop feedback system, at least one sensor (not shown) that senses a symptom of the body can be a part of the therapy delivery device 12 or, alternatively, remotely placed at a bodily location.

Figure 13:
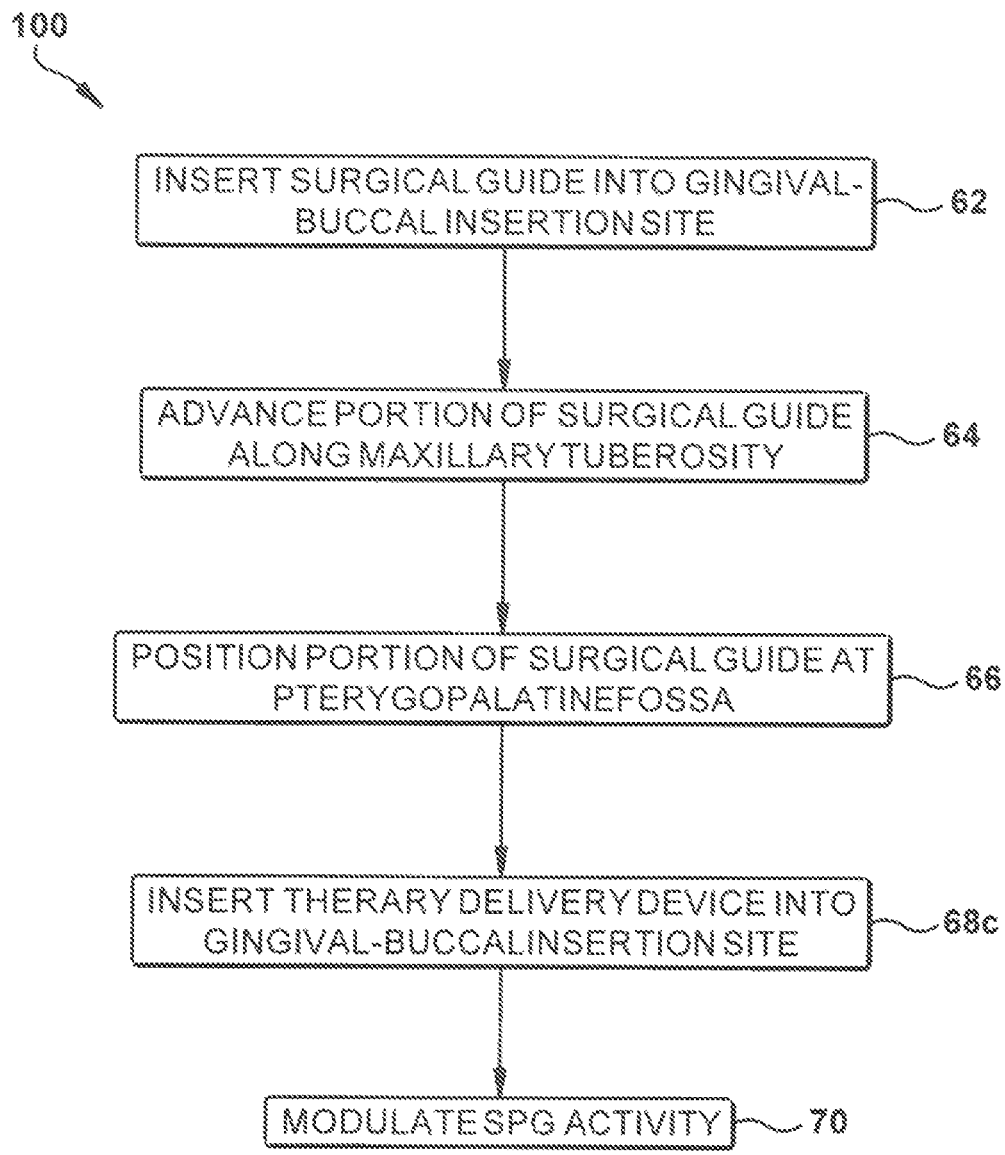
FIG. 13 is a process flow chart illustrating a method for treating a medical condition in a subject according to another aspect of the present invention.

FIG. 13 illustrates a method 100 for treating a medical condition (e.g., headache) in a subject according to another aspect of the present invention. In FIG. 13, steps that are identical as steps in FIG. 4 use the same reference numbers, whereas steps that are similar but not identical carry the suffix "c".

Figure 14:
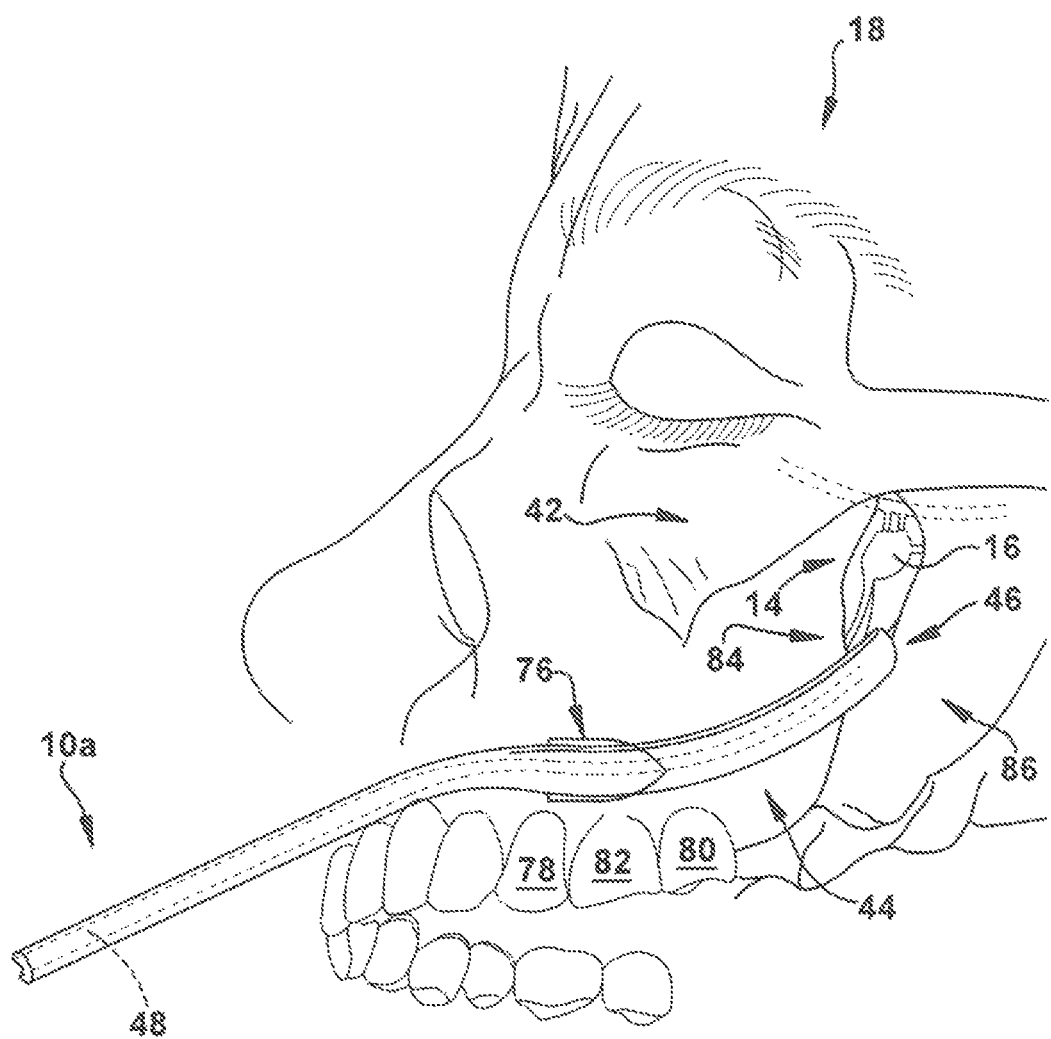
FIG. 14 is a perspective view showing a distal end portion of a surgical guide (FIGS. 2A-D) engaging the junction formed by the posterior maxillary buttress and the pterygoid plate.

The method 100 can begin by assessing the neuroanatomy of the subject to determine the size and location of the PPF 14 (as described above). Based at least in part on the subject's neuroanatomy, a properly-sized surgical guide $10_a$ (FIGS. 2A-D) can be selected. As shown in FIG. 14, a gingival-buccal insertion site 76 can be formed by creating an incision of about 0.5 cm to about 1.5 cm that extends between the first 78, second 82, and/or third 80 molars and is substantially parallel to the gum line (e.g., about 3-5 mm superior to the mucogingival junction).

At Step 62, the distal end portion $28_a$ of the surgical guide $10_a$ can be inserted into the gingival-buccal insertion site 76 and advanced in a posterior direction so that the third surface $38_a$ traverses under the zygomatic bone 42 along the maxillary tuberosity 44. The surgical guide $10_a$ can then be further advanced at Step 64 until the distal tip 46 engages the junction formed by the posterior maxillary buttress 84 and the pterygoid plate 86, just inferior to the PPF 14.

Advancement of the surgical guide $10_a$ may naturally stop when the distal tip 46 is correctly positioned at the junction formed by the posterior maxillary buttress 84 and the pterygoid plate 86. At this point, the surgical guide $10_a$ can be rotated in a superior direction until the distal tip 46 is within the PPF 14 (Step 66). This can be done by carefully "walking" the distal tip 46 up the pterygoid plate 86 until the distal tip (or other desired portion of the surgical guide) slides into the PPF 14.

Figure 15:
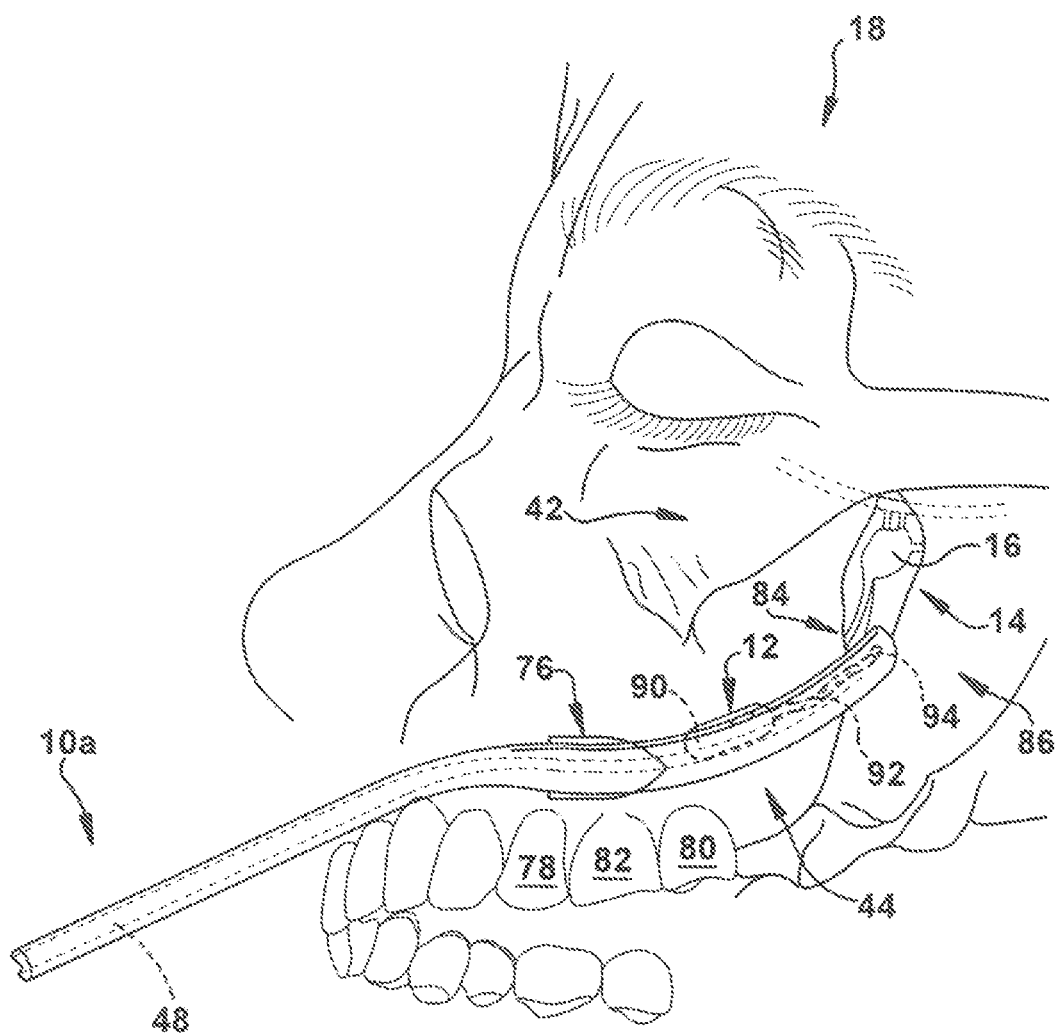
FIG. 15 is a perspective view showing a therapy delivery device being advanced along a groove of the surgical guide in FIG. 14.
Figure 16:
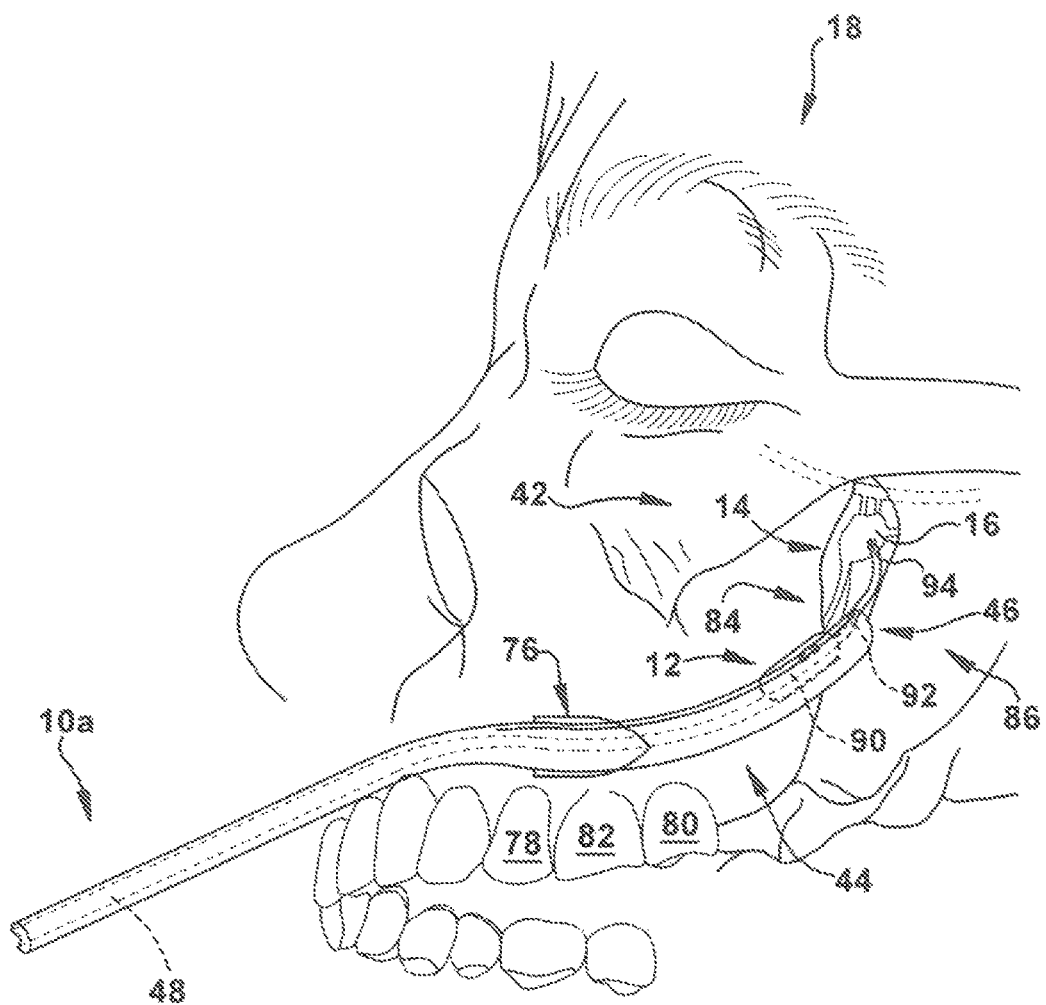
FIG. 16 is a perspective view showing the therapy delivery device in FIG. 15 positioned about the PPF.

At Step $68_c$, a therapy delivery device 12, such as the neurostimulator described above can be inserted into the gingival-buccal insertion site 76 by first mating the neurostimulator with the groove 48 of the surgical guide $10_c$. The neurostimulator can then be urged into the buccal-gingival insertion site 76 and advanced along the groove 48 by applying tactile force to the neurostimulator. Tactile force can be continuously applied to the neurostimulator so that the neurostimulator progressively moves along the groove 48 towards the distal tip 46 of the surgical guide $10_a$ (FIG. 15). As the neurostimulator approaches the distal tip 46 of the surgical guide $10_a$, the increasingly shallow groove 48 causes the neurostimulator to disengage from the surgical guide and be positioned on or proximate to the PPF 14 (FIG. 16).

The position of the neurostimulator can then be adjusted, if needed, so that the electrode(s) 94 is/are positioned on or proximate all or only a portion of the target site (i.e., the SPG 16). If it has not been done so already, the electrode(s) 94 and the controller 90 can be securely anchored so that the electrical signal delivered by the electrode(s) 94 will consistently modulate the same region(s) of the SPG 16.

At Step 70, an electrical signal can be delivered to the electrode(s) 94 so that the electrical signal is directly applied to the SPG 16. As described above, delivery of the electrical signal to the SPG 16 can modulate SPG activity and thereby lead to pain intensity reduction in the subject. Upon delivery of the electrical signal to the electrode(s) 94, the subject may be asked to report any sensation, such as pain or paresthesia. The position of the electrical lead 92 or the frequency of electrical energy being delivered to the electrode(s) 94 may then be adjusted until the subject reports that the stimulation is comfortable or has caused a substantial reduction in pain intensity. After successful implantation of the neurostimulator, the subject (or a medical professional) can alter the electrical signal at the earliest onset of pain.

Figure 17:
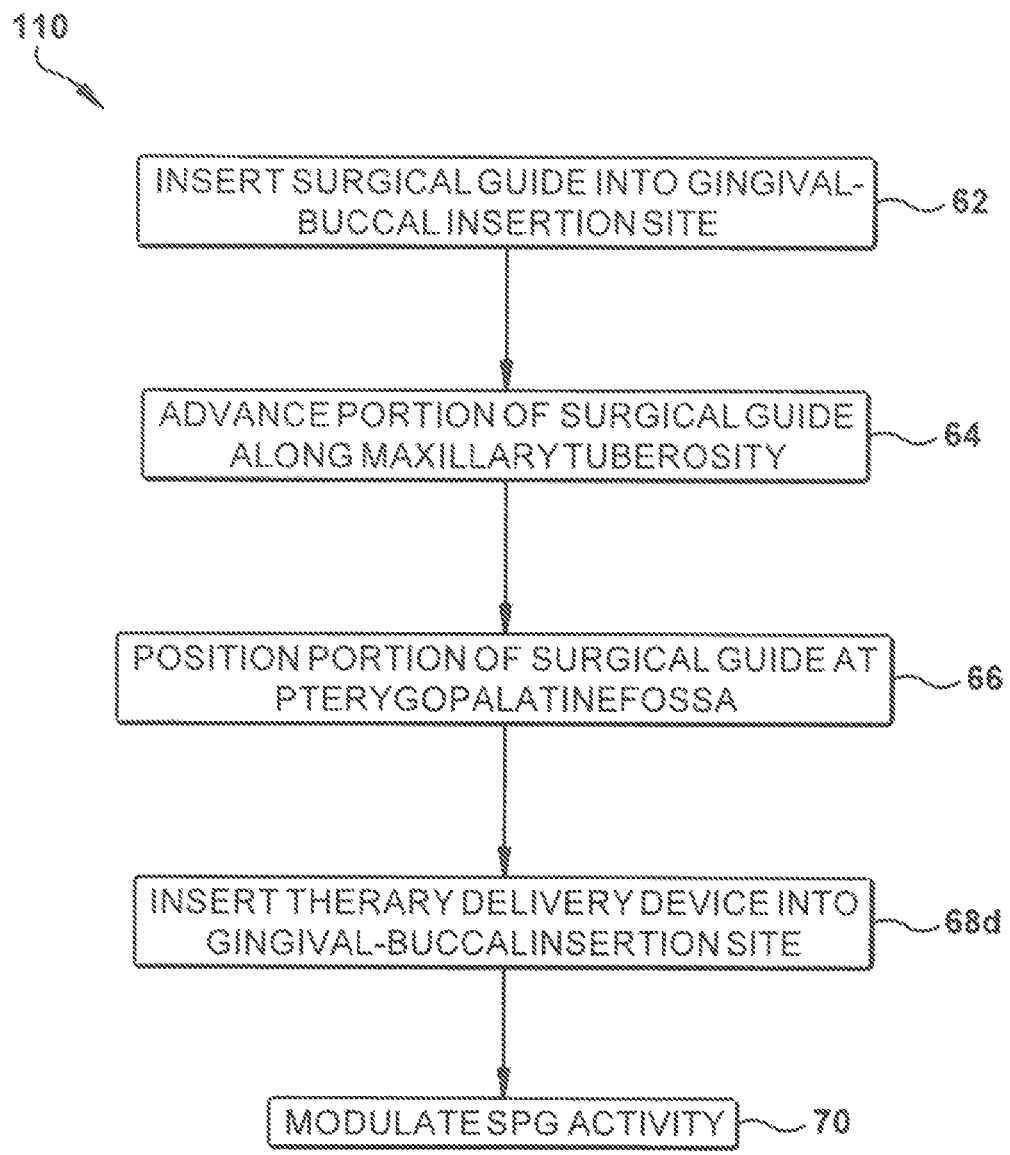
FIG. 17 is a process flow chart illustrating a method for treating a medical condition in a subject according to another aspect of the present invention.

FIG. 17 illustrates a method 110 for treating a medical condition (e.g., headache) in a subject according to another aspect of the present invention. In FIG. 17, steps that are identical as steps in FIG. 4 use the same reference numbers, whereas steps that are similar but not identical carry the suffix "d".

Figure 18:
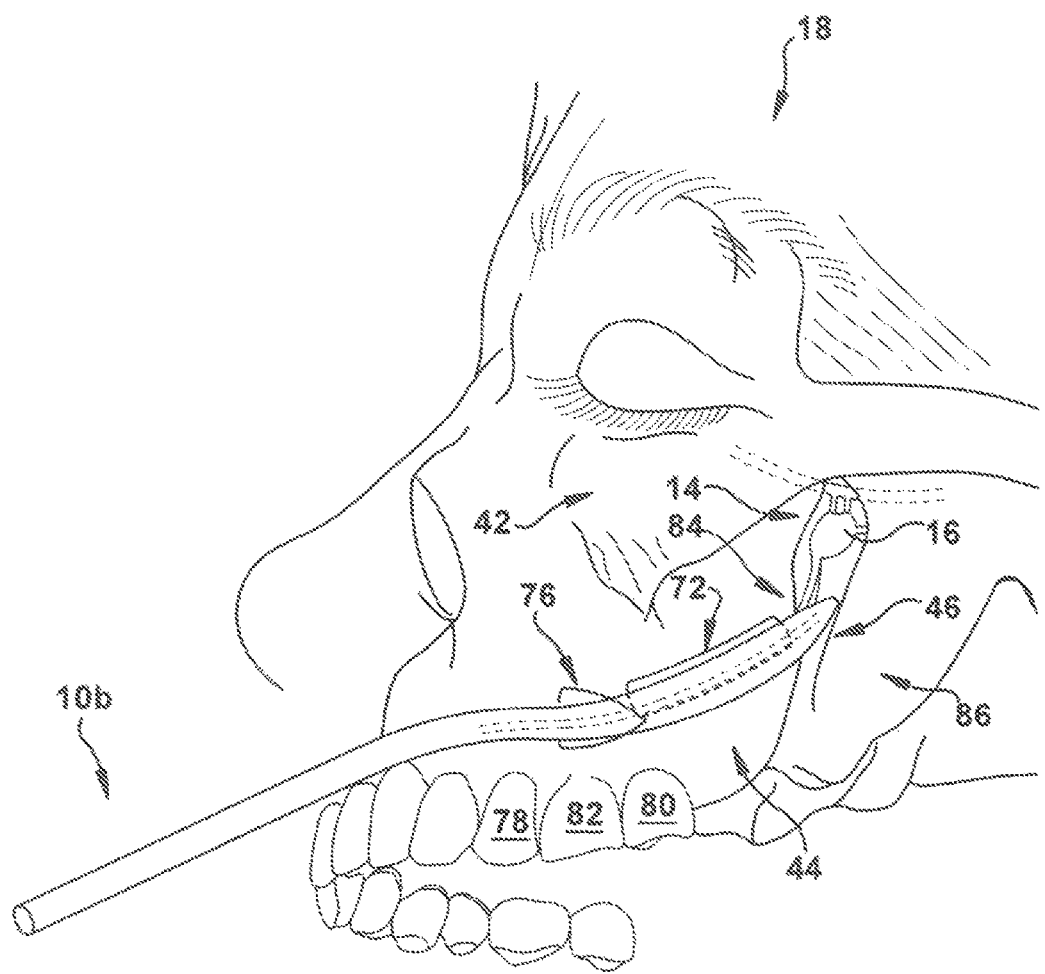
FIG. 18 is a perspective view showing a distal end portion of a surgical guide (FIG. 3) engaging the junction formed by the posterior maxillary buttress and the pterygoid plate.

The method 110 can begin by assessing the neuroanatomy of the subject to determine the size and location of the PPF 14 (as described above). Based at least in part on the subject's neuroanatomy, a properly-sized surgical guide $10_b$ (FIG. 3) can be selected. As shown in FIG. 18, a gingival-buccal insertion site 76 can be formed by creating an incision of about 0.5 cm to about 1.5 cm that extends between the first 78, second 82, and/or third 80 molars and is substantially parallel to the gum line (e.g., about 3-5 mm superior to the mucogingival junction).

At Step 62, the distal end portion $28_b$ of the surgical guide $10_b$ can be inserted into the gingival-buccal insertion site 76. The surgical guide $10_b$ can then be advanced in a posterior direction so that the third surface $38_b$ traverses under the zygomatic bone 42 along the maxillary tuberosity 44 (Step 64). Next, the surgical guide $10_b$ can be further advanced until the distal tip 46 engages the junction formed by the posterior maxillary buttress 84 and the pterygoid plate 86, just inferior to the PPF 14.

Advancement of the surgical guide $10_b$ may naturally stop when the distal tip 46 is correctly positioned at the junction formed by the posterior maxillary buttress 84 and the pterygoid plate 86. At this point, the surgical guide $10_b$ can be rotated in a superior direction until the distal tip 46 is within the PPF 14 (Step 66). This can be done by carefully "walking" the distal tip 46 up the pterygoid plate 86 until the distal tip (or other desired portion of the surgical guide) slides into the PPF 14.

Figure 19:
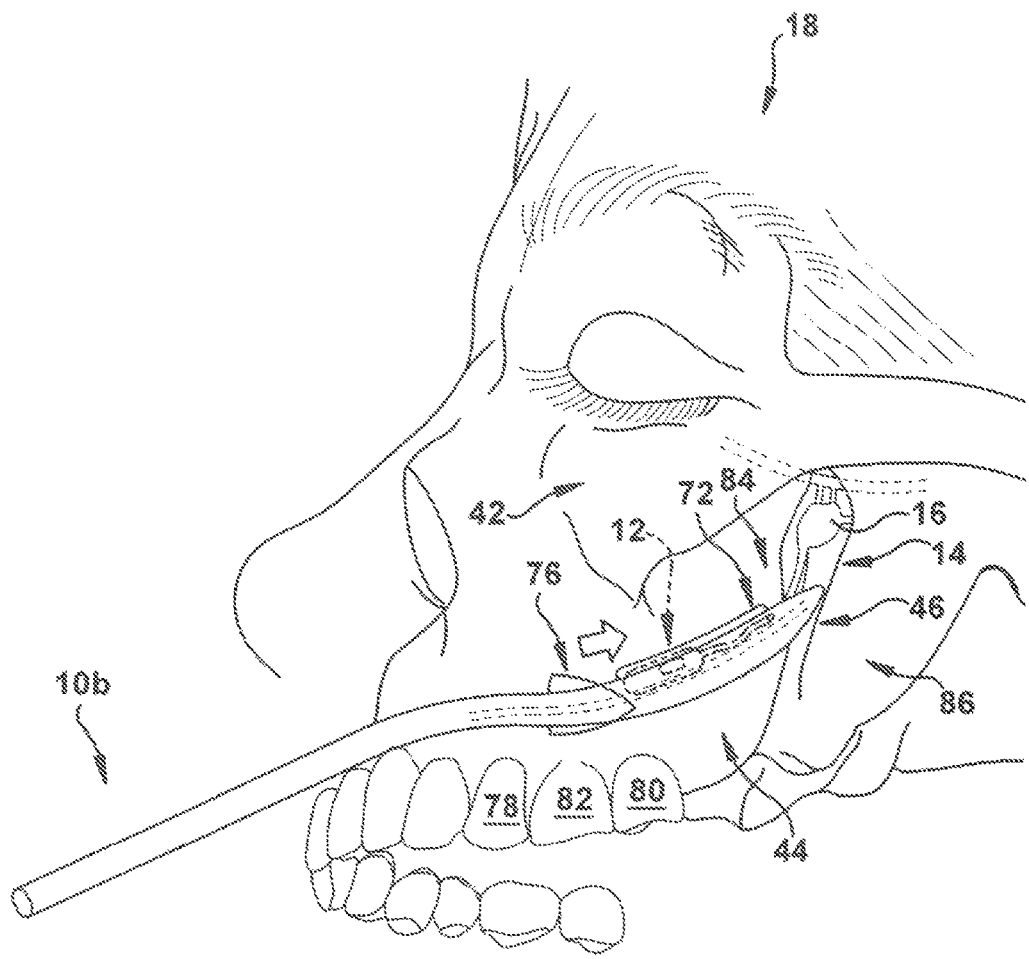
FIG. 19 is a perspective view showing a therapy delivery device being loaded onto a trough member of the surgical guide in FIG. 18.
Figure 20:
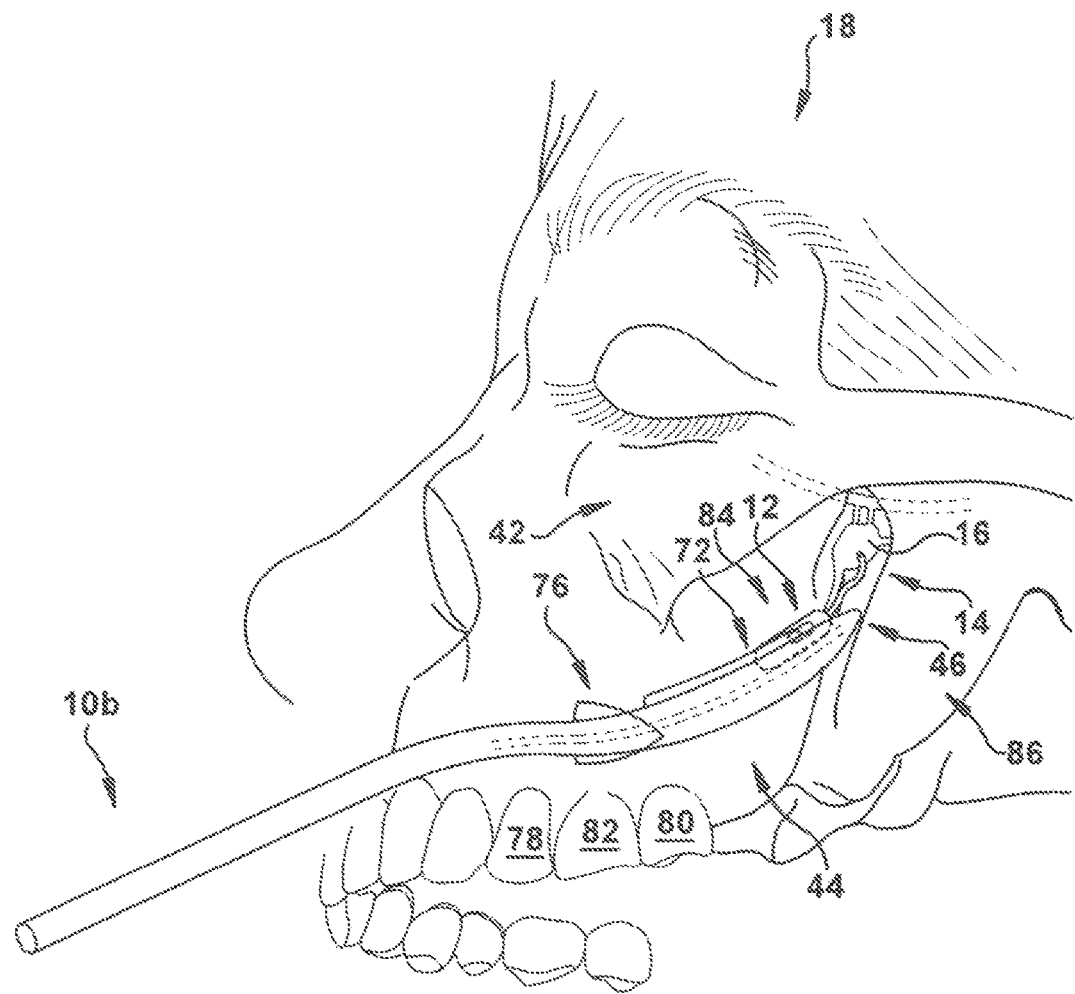
FIG. 20 is a perspective view showing the therapy delivery device in FIG. 19 positioned about the PPF.
Figure 21:
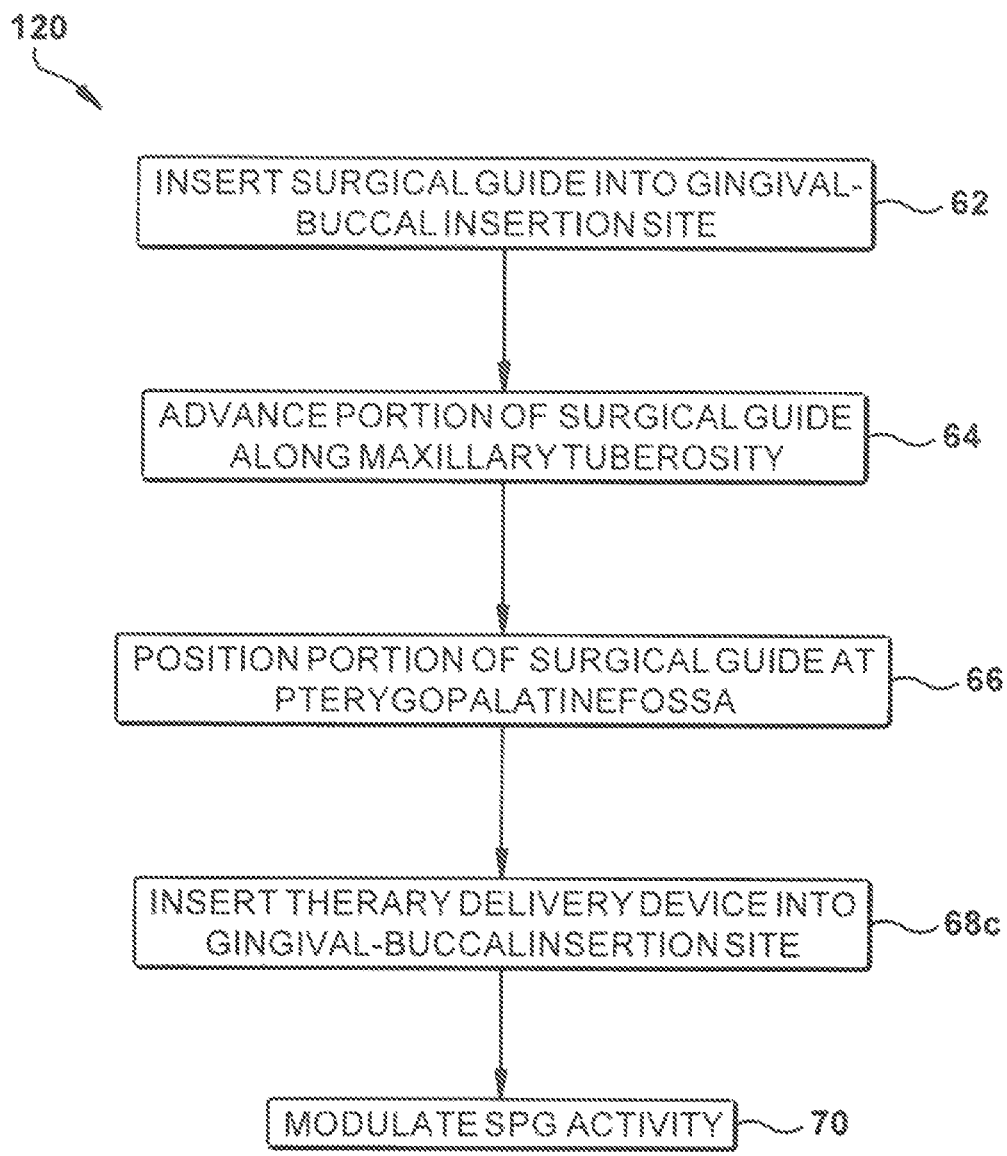
FIG. 21 is a process flow chart illustrating a method for treating a medical condition in a subject according to another aspect of the present invention.

At Step $68_d$, a therapy delivery device 12, such as the neurostimulator described above can be inserted into the gingival-buccal insertion site 76 by loading the neurostimulator onto the trough member 72 (FIG. 19). Next, the neurostimulator can be advanced into the buccal-gingival insertion site 76 (indicated by arrow) and through the tunnel 88 by applying tactile force to the trough member 72 and/or neurostimulator. Tactile force can be continuously applied so that the trough member 72 is slowly moved across the third surface $38_b$ of the surgical guide $10_b$ towards the distal tip 46. Force can be applied until the electrode(s) 94 is/are positioned on or proximate the PPF 14 (FIG. 20).

The position of the neurostimulator can then be adjusted, if needed, so that the electrode(s) 94 is/are positioned on or proximate all or a portion of the target site (i.e., the SPG 16). If it has not already been done, the electrode(s) 94 and the controller 90 can be securely anchored so that the electrical signal delivered by the electrode(s) will consistently modulate the same region(s) of the SPG 16.

At Step 70, an electrical signal can be delivered to the electrode(s) 94 so that the electrical signal is directly applied to the SPG 16. As described above, delivery of the electrical signal to the SPG 16 can modulate SPG activity and thereby lead to pain intensity reduction in the subject. Upon delivery of the electrical signal to the electrode(s) 94, the subject may be asked to report any sensation, such as pain or paresthesia. The position of the electrical lead 92 or the frequency of electrical energy being delivered to the electrode(s) 94 may then be adjusted until the subject reports that the stimulation is comfortable or has caused a substantial reduction in pain intensity. After successful implantation of the neurostimulator, the subject (or a medical professional) can alter the electrical signal at the earliest onset of pain.

Figure 22:
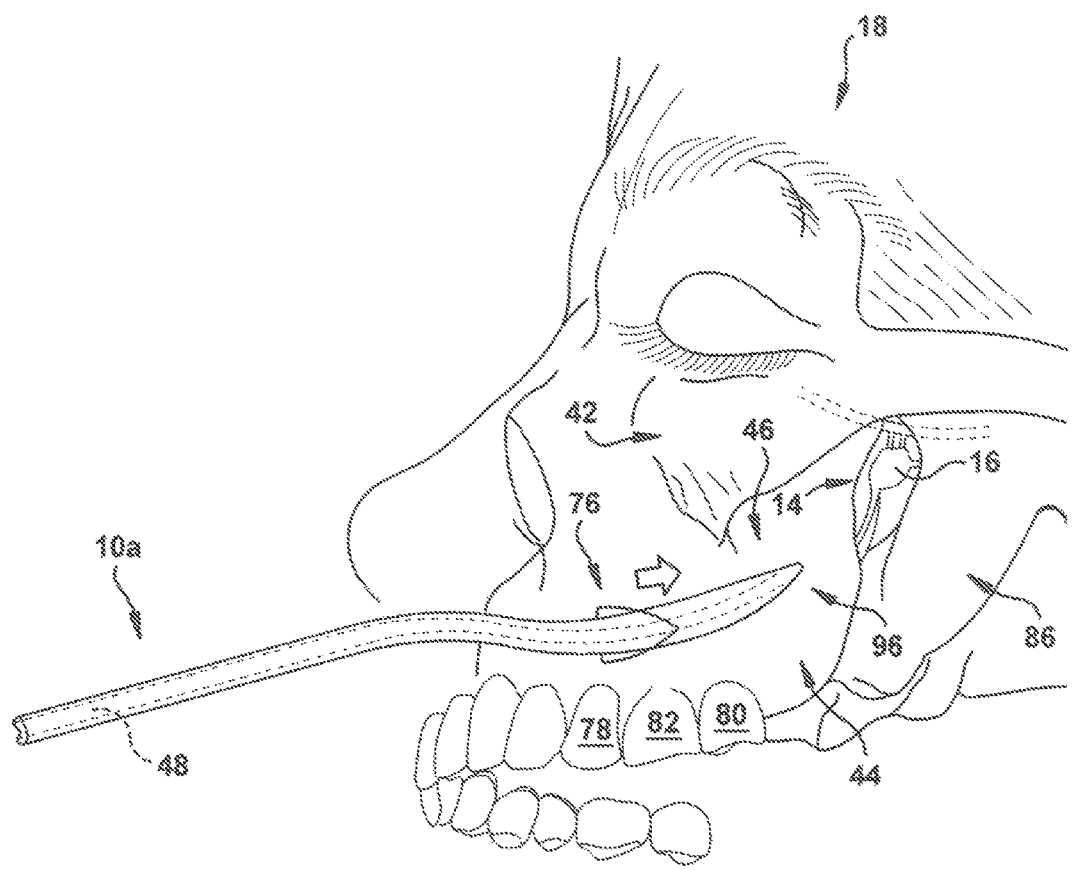
FIG. 22 is a perspective view showing a distal end portion of a surgical guide (FIGS. 2A-D) engaging the posterior maxilla.

FIG. 22 illustrates a method 120 for treating a medical condition (e.g., headache) in a subject according to another aspect of the present invention. In FIG. 22, steps that are identical as steps in FIG. 4 use the same reference numbers, whereas steps that are similar but not identical carry the suffix "e".

The method 120 can begin by assessing the neuroanatomy of the subject to determine the size and location of the PPF 14 (as described above). Based at least in part on the subject's neuroanatomy, a properly-sized surgical guide $10_a$ (FIGS. 2A-D) can be selected. It will be appreciated that any of the other surgical guides 10 and $10_b$ described above may be used with the method. As shown in FIG. 22, a gingival-buccal insertion site 76 can be formed by creating an incision of about 0.5 cm to about 1.5 cm that extends between the first 78, second 82, and/or third 80 molars and is substantially parallel to the gum line (e.g., about 3-5 mm superior to the mucogingival junction).

At Step 62, the distal end portion $28_a$ of the surgical guide $10_a$ can be inserted into the gingival-buccal insertion site 76. The surgical guide $10_a$ can then be advanced under image guidance (e.g., fluoroscopy or CT) into contact with the posterior maxilla 96 (FIG. 22). Contact between the distal end portion $28_a$ and the posterior maxilla 96 can be maintained as the surgical guide $10_a$ is advanced in a superior, medial, and posterior direction to the PPF 14 (Step 122). At Step $66_e$, the distal end portion $28_a$ can be advanced until the distal tip 46 is positioned within the PPF 14. Advantageously, advancement of the surgical guide $10_a$ across the posterior maxilla 96 to the PPF 14 allows for less tissue dissection, less tissue trauma, and fewer complications from bleeding and hematomas, for example.

Figure 23:
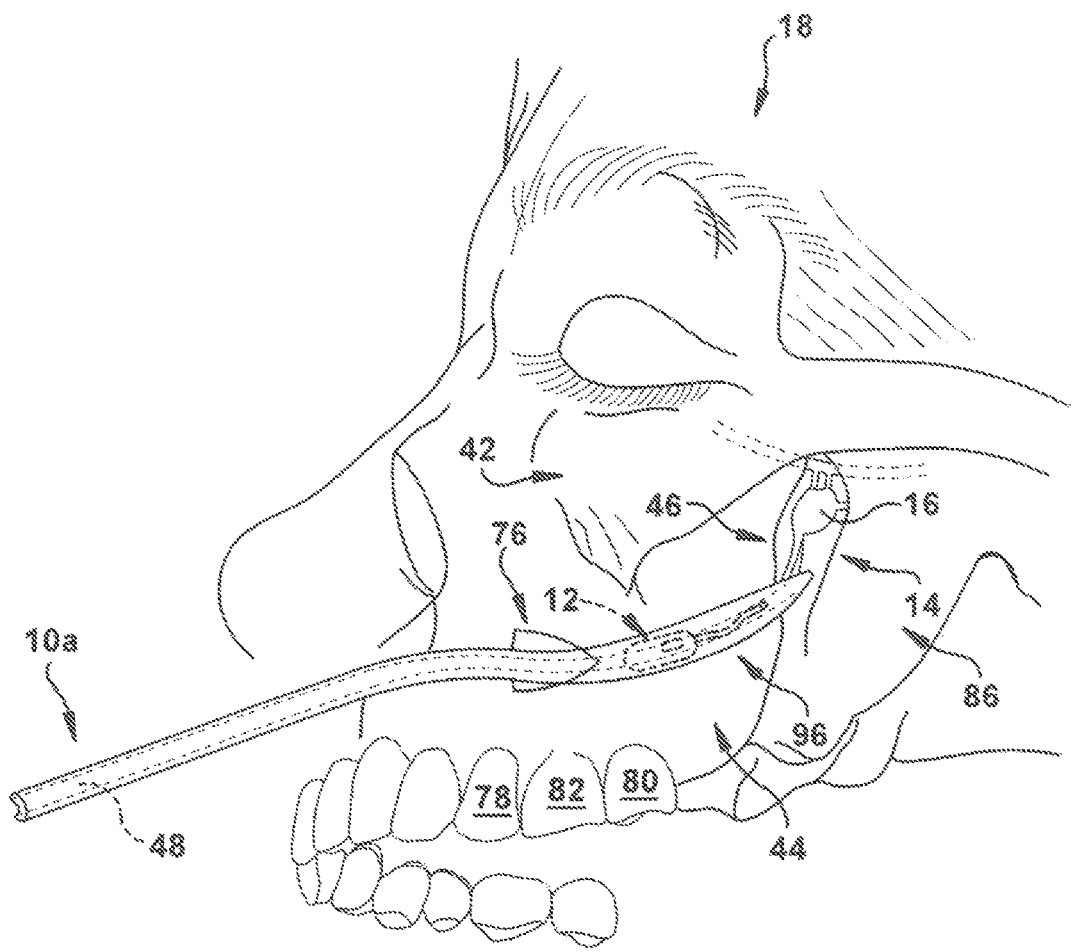
FIG. 23 is a perspective view showing a therapy delivery device being advanced along a groove of the surgical guide in FIG. 22.
Figure 24:
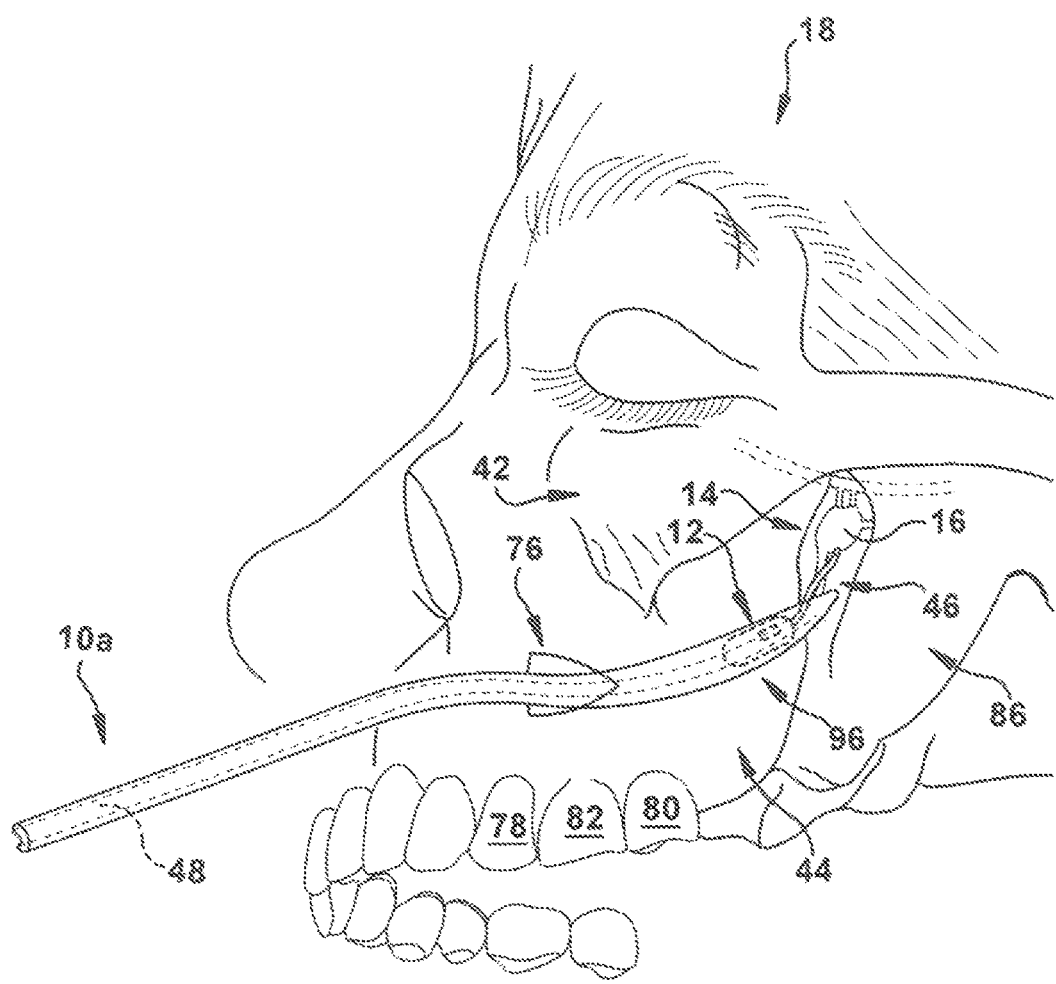
FIG. 24 is a perspective view showing the therapy delivery device in FIG. 23 positioned about the PPF.

After appropriately positioning the surgical guide $10_a$, a therapy delivery device 12, such as the neurostimulator described above can be inserted into the gingival-buccal insertion site 76 by first mating the neurostimulator with the groove 48 of the therapy delivery device (as described above) (Step $68_c$). The neurostimulator can then be urged into the gingival-buccal insertion site 76 and advanced along the groove 48 by applying tactile force to the neurostimulator (FIG. 23). Tactile force can be continuously applied to the neurostimulator so that the neurostimulator is progressively moved along the groove 48 towards the distal tip 46. As the neurostimulator approaches the distal tip 46 of the surgical guide $10_a$, the increasingly shallow groove 48 causes the neurostimulator to disengage from the surgical guide and be positioned on or proximate to the PPF 14 (FIG. 24).

The position of the neurostimulator can then be adjusted, if needed, so that the electrode(s) 94 is/are positioned on or proximate all or only a portion of the target site (i.e., the SPG 16). If it has not been done so already, the electrode(s) 94 and the controller 90 can be securely anchored so that the electrical signal delivered by the electrode(s) will consistently modulate the same region(s) of the SPG 16.

At Step 70, an electrical signal can be delivered to the electrode(s) 94 so that the electrical signal is directly applied to the SPG 16. As described above, delivery of the electrical signal to the SPG 16 can modulate SPG activity and thereby lead to pain intensity reduction in the subject. Upon delivery of the electrical signal to the electrode(s) 94, the subject may be asked to report any sensation, such as pain or paresthesia. The position of the electrical lead 92 or the frequency of electrical energy being delivered to the electrode(s) 94 may then be adjusted until the subject reports that the stimulation is comfortable or has caused a substantial reduction in pain intensity. After successful implantation of the neurostimulator, the subject (or a medical professional) can alter the electrical signal at the earliest onset of pain.

From the above description of the invention, those skilled in the art will perceive improvements, changes and modifications. For example, it will be appreciated that the methods 60, 100, 110, and 120 of the present invention can be applied to one or both sides of a subject's head 18. Additionally, it will be appreciated that therapy delivery devices 12 may be placed permanently or temporarily at a target site (e.g., the SPG 16) to provide chronic or acute neuromodulation. Such improvements, changes, and modifications are within the skill of the art and are intended to be covered by the appended claims.

Having described the invention, I claim:

1. A method of delivering a neurostimulator to within close proximity of a sphenopalatine ganglion (SPG), comprising:
   making an incision over a skull;
   inserting a surgical guide into the incision;
   advancing the surgical guide under a zygomatic bone along a maxillary tuberosity towards a PPF; and
   delivering the neurostimulator in close proximity to the SPG.

2. The method of claim 1, wherein said advancing step further comprises advancing the surgical guide until a distal tip of the surgical guide engages a junction formed by a posterior maxillary buttress and a pterygoid plate.

3. The method of claim 2 further comprising rotating the surgical guide in a superior direction until the distal tip is within the PPF.

4. The method of claim 1, wherein the incision is made at a gingival-buccal insertion site.

5. The method of claim 1, wherein the neurostimulator is delivered in close proximity to the SPG from the surgical guide.

6. The method of claim 1, wherein the surgical guide that is inserted into the incision comprises a curvilinear body having the distal end portion, a proximal end portion, and an intermediate portion extending between the distal and proximal end portions, the proximal end portion being defined by oppositely disposed first and second surfaces and the distal end portion being defined by oppositely disposed third and fourth surfaces, the proximal end portion and the intermediate portion defining a longitudinal plane extending between the proximal and distal end portions, the distal end portion having an arcuate configuration relative to the longitudinal plane, the body including a groove that extends between the proximal and distal end portions and is embedded in at least a portion of each of the first and third surfaces, wherein the curvilinear body comprises a bottom edge that extends between a proximal end and a distal end of the groove and is opposite a top edge of the groove, the groove having a first depth within the body at the proximal end of the groove and a second depth within the body at the distal end of the groove, the first depth being closer to the bottom edge of the body and being greater than the second depth.

7. The method of claim 1, wherein the surgical guide is inserted into the incision without penetrating the palate of the subject.

8. A method of treating a neurological disorder, comprising:
    making an incision over a skull;
    inserting a surgical guide into the incision;
    advancing the surgical guide under a zygomatic bone along a maxillary tuberosity towards a pterygopalatine fossa (PPF);
    delivering a neurostimulator in close proximity to the sphenopalatine ganglion (SPG); and
    applying an electrical current from the neurostimulator to the SPG to treat the neurological disorder.

9. The method of claim 8, wherein the neurological disorder is headache.

10. The method of claim 8, wherein the surgical guide that is inserted into the incision comprises a curvilinear body having the distal end portion, a proximal end portion, and an intermediate portion extending between the distal and proximal end portions, the proximal end portion being defined by oppositely disposed first and second surfaces and the distal end portion being defined by oppositely disposed third and fourth surfaces, the proximal end portion and the intermediate portion defining a longitudinal plane extending between the proximal and distal end portions, the distal end portion having an arcuate configuration relative to the longitudinal plane, the body including a groove that extends between the proximal and distal end portions and is embedded in at least a portion of each of the first and third surfaces, wherein the curvilinear body comprises a bottom edge that extends between a proximal end and a distal end of the groove and is opposite a top edge of the groove, the groove having a first depth within the body at the proximal end of the groove and a second depth within the body at the distal end of the groove, the first depth being closer to the bottom edge of the body and being greater than the second depth.

11. The method of claim 8, wherein said advancing step further comprises advancing the surgical guide until a distal tip of the surgical guide engages a junction formed by a posterior maxillary buttress and a pterygoid plate.

12. The method of claim 8 further comprising rotating the surgical guide in a superior direction until the distal tip is within the PPF.

13. The method of claim 8, wherein the incision is made at a gingival-buccal insertion site.

14. The method of claim 8, wherein the neurostimulator is delivered in close proximity to the SPG from the surgical guide.

15. A method of obtaining treatment of a neurological disorder, comprising:
    receiving an incision over a skull;
    receiving a surgical guide through the incision;
    receiving the surgical guide under a zygomatic bone along a maxillary tuberosity towards a pterygopalatine fossa (PPF);
    receiving a neurostimulator in close proximity to the sphenopalatine ganglion (SPG); and
    receiving an electrical current from the neurostimulator to the SPG to obtain treatment of the neurological disorder.

16. The method of claim 15, wherein the neurological disorder is headache.

17. The method of claim 15, wherein the surgical guide that is received through the incision comprises a curvilinear body having the distal end portion, a proximal end portion, and an intermediate portion extending between the distal and proximal end portions, the proximal end portion being defined by oppositely disposed first and second surfaces and the distal end portion being defined by oppositely disposed third and fourth surfaces, the proximal end portion and the intermediate portion defining a longitudinal plane extending between the proximal and distal end portions, the distal end portion having an arcuate configuration relative to the longitudinal plane, the body including a groove that extends between the proximal and distal end portions and is embedded in at least a portion of each of the first and third surfaces, wherein the curvilinear body comprises a bottom edge that extends between a proximal end and a distal end of the groove and is opposite a top edge of the groove, the groove having a first depth within the body at the proximal end of the groove and a second depth within the body at the distal end of the groove, the first depth being closer to the bottom edge of the body and being greater than the second depth.

18. The method of claim 15, wherein the surgical guide is received through the incision without penetrating the palate of the subject.

19. The method of claim 15, wherein receiving the surgical guide under a zygomatic bone along a maxillary tuberosity towards a PPF comprises receiving the surgical guide until a distal tip of the surgical guide engages a junction formed by a posterior maxillary buttress and a pterygoid plate.

20. The method of claim 15, further comprising receiving the surgical guide after rotation of the surgical guide in a superior direction until the distal tip is within the PPF.

21. The method of claim 15, wherein the incision is received at a gingival-buccal insertion site.

22. The method of claim 15, wherein the neurostimulator is received in close proximity to the SPG from the surgical guide.

23. A method of obtaining treatment of a neurological disorder in a subject, comprising:
    receiving an incision over a skull of the subject;
    receiving a surgical guide through the incision;
    receiving the surgical guide under a zygomatic bone along a maxillary tuberosity towards a pterygopalatine fossa (PPF);
    receiving a neurostimulator in close proximity to the sphenopalatine ganglion (SPG);
    receiving an electrical current from the neurostimulator to the SPG to obtain treatment of the neurological disorder; and
    applying, by the subject, an electrical current from the neurostimulator to the SPG to treat the neurological disorder.

24. The method of claim 23, wherein the neurological disorder is headache.

25. The method of claim 23, wherein the surgical guide that is received through the incision comprises a curvilinear body having the distal end portion, a proximal end portion, and an intermediate portion extending between the distal and proximal end portions, the proximal end portion being defined by oppositely disposed first and second surfaces and the distal end portion being defined by oppositely disposed third and fourth surfaces, the proximal end portion and the intermediate portion defining a longitudinal plane extending between the proximal and distal end portions, the distal end portion having an arcuate configuration relative to the longitudinal plane, the body including a groove that extends between the proximal and distal end portions and is embedded in at least a portion of each of the first and third surfaces, wherein the curvilinear body comprises a bottom edge that extends between a proximal end and a distal end of the groove and is opposite a top edge of the groove, the groove having a first depth within the body at the proximal end of the groove and a second depth within the body at the distal end of the groove, the first depth being closer to the bottom edge of the body and being greater than the second depth.

26. The method of claim 23, wherein the surgical guide is received through the incision without penetrating the palate of the subject.

27. The method of claim 23, wherein receiving the surgical guide under a zygomatic bone along a maxillary tuberosity towards a PPF comprises receiving the surgical guide until a distal tip of the surgical guide engages a junction formed by a posterior maxillary buttress and a pterygoid plate.

28. The method of claim 23, further comprising receiving the surgical guide after rotation of the surgical guide in a superior direction until the distal tip is within the PPF.

29. The method of claim 23, wherein the incision is received at a gingival-buccal insertion site.

30. The method of claim 23, wherein the neurostimulator is received in close proximity to the SPG from the surgical guide.

\* \* \* \* \*